US005759788A

United States Patent [19]
Fremeau, Jr. et al.

[11] Patent Number: 5,759,788
[45] Date of Patent: Jun. 2, 1998

[54] HIGH AFFINITY L-PROLINE TRANSPORTER POLYPEPTIDES; ANTIBODIES AND IMMUNOASSAYS SPECIFIC FOR THEM

[75] Inventors: Robert T. Fremeau, Jr.; Marc G. Caron, both of Durham, N.C.; Randy D. Blakely, Stone Mountain, Ga.

[73] Assignees: Emory University, Atlanta, Ga.; Duke University, Durham, N.C.

[21] Appl. No.: 753,985

[22] Filed: Dec. 3, 1996

Related U.S. Application Data

[62] Division of Ser. No. 879,617, May 1, 1992, Pat. No. 5,580,775.

[51] Int. Cl.$^6$ .................. C07K 14/705; G01N 33/53
[52] U.S. Cl. ............ 435/7.21; 530/350; 530/388.2; 530/389.1; 435/7.1; 435/69.1
[58] Field of Search ................. 530/350, 388.2, 530/389.1; 435/69.1, 7.1, 7.21

[56] References Cited

U.S. PATENT DOCUMENTS

| | | | |
|---|---|---|---|
| 4,873,191 | 10/1989 | Wagner et al. | |
| 5,312,734 | 5/1994 | Uhl et al. | 435/69.1 |
| 5,552,308 | 9/1996 | Hoffman et al. | 435/172.3 |

OTHER PUBLICATIONS

Askew et al "Molecular Recognition with Convergent Functional Groups Synthetic and Structural Studies with a Model Receptor for Nucleic Acid Components," *J. Am. Chem. Soc.* 111, 1082–1090 (1989).

Bolcer, et al., "Transport of L–Proline by Rat Brain Siloes," *Brain Res.* 102, 143–151 (1976).

Bennett, et al., "Amino Acid Neurotransmitter Candidates: Sodium–Dependent High–Affinity Uptake by Unique Synaptosomal Fractions," *Science* 178, No. 4056, pp. 997–999 (1972).

Blakely, et al., "Cloning and Expression of a Functional Serotonin Transporter from Rat Brain," *Nature* 354, 66–70 (1991).

Blakely, et al., Distinct Developmentally Regulated Brain mRNAs Direct the Synthesis of Neurotransmitter Transporters, *Journal of Neurochemistry*, vol. 56, No. 1, pp. 860–871 (Jan. 1991).

Capecchi, "The New Mouse Genetics Altering the Genome by Gene Targeting," *Trends in Genetics*, vol. 5, pp. 70–76 (1989).

Capecchi "A Strategy for Generating Mice of Any Desired Genotype Through Gene Targeting," *Cell Biology*, Thursday, 2 Feb.: Afternoon Symposia (26–32), No. 3729.

Davis, et al., *Advanced Bacterial Genetics* (Cold Spring Harbor Laboratory, Cold Spring Harbor, N.Y.) (1980) (Table of Contents Only).

(List continued on next page.)

*Primary Examiner*—David L. Fitzgerald
*Attorney, Agent, or Firm*—Kilpatrick Stockton LLP

[57] ABSTRACT

The anatomical distribution, nucleic acid sequence, pharmacological properties, and inferred structural features of a cDNA encoding a high affinity, Na$^+$-dependent rat brain L-proline transporter is described. The expression of this carrier in subpopulations of putative glutamatergic pathways supports a specific role for L-proline in excitatory amino acid neurotransmission. The cloned transporter cDNA predicts a 637 amino acid protein with 12 putative transmembrane domains and exhibits 44%–45% amino acid sequence identity with other neurotransmitter transporters. These findings support a synaptic role for L-proline in specific excitatory pathways in the CNS. The sequence can be used for expression of the transporter molecule, to make probes for the same protein from other species and related proteins, in diagnostic assays, and to design functional and structural analogs for use in research and possible clinical treatments. The protein is useful in making antibodies, conducting research studies, and design of therapeutic transporter modulators for clinical treatments.

14 Claims, 6 Drawing Sheets

OTHER PUBLICATIONS

Fremeau and Popko, "In Situ Analysis of Myelin Basic Protein Gene Expression to Myelin–Deficient Oligodendrocytes: Antisense hnRNA and Readthrough Transcription," *The EMBO Journal*, vol. 9, No. 11, pp. 3533–3538 (1990).

Fuerst et al "Eukaryotic Transient–Expression System Based on Recombinant Vaccinia Virus that Synthesizes Bacteriophage T7 RNA Polymerase," *Proc. Natl. Acad. Sci. USA* 83, 8122–8126 (1986).

Giros, et al., "Cloning and Functional Characterization of a Cocaine–Sensitive Dopamine Transporter," *FEBS Lett.* 295, 149–154 (1991).

Graham and VanDer, "A New Technique for the Assay of Infectivity of Human Adenovirus 5 DNA," *Virology* 52, 456 (1973).

Hammer, et al. "Spontaneous Inflammatory Disease in Transgenic Rats Expressing HLA–B27 and Human $\beta_2$m: An Animal Model of HLA–B27–Associated Human Disorders," *Cell* 63:1099–112 (1990).

Hammerman and Sacktor, "Transport of Amino Acids in Renal Brush Border Membrane Vesicles" *J. Biol. Chem* 252, 591–595 (1977).

Hauptmann, et al., "High Affinity Proline Uptake in Rat Brain Synaptosomes," *FEBS* 0815 vol. 161, No. 2 (Sep. 1983).

Hoffman, et al., "Cloning of a Serotonin Transporter Affected by Antidepressants," *Science* 254, 579–580 (1991).

Hogan, et al., Manipulating the Mouse Embryo, Cold Spring Harbor Laboratory, Cold Spring Harbor, New York (1986) (Table of Contents Only).

Hollman, et al., "Cloning by Functional Expression of a Member of the Glutamate Receptor Family," *Nature* 342, 643–645 (1989).

Hwang, et al., "Uptake of L–[$^{14}$C] Proline by Isolated Rat Brain Capillaries," *J. Neurochem.* 40, 317–323 (1983).

Joynet, et al., "Production of Mutation in Mouse En–2 Gene by Homoglous Recombination in Embryonic Stem Cells" *Nature* 338, 153–156 (1989).

Kanner and Sharon, "Active Transport of I–Proline by Membrane Vesicles Isolated from Rat Brain," *Biochim Biophys Acta* 600, 185–194 (1980).

Kennelly and Krebs, "Consensus Sequences as Substrate Specificity Determinants for Protein Kinases and Protein Phosphatases," *J. Biol. Chem.* 266, 15555–15558 (1991).

Kimura et al "Isolation and Characterization of Temperature–Sensitive Mutants of Simian Virus 40," *Virology* 49, 394 (1972).

Kozak, M. "An Analysis of 5'–noncoding Sequences from 699 Vertebrate Messenger RNAs," *Nucleic Acids Research*, vol. 15, No. 20 (Oct. 26, 1987).

Kuhar and Murrin, "Sodium–Dependent, High Affinity Choline Uptake," *J. Neurochem.* 30 15–21 (1978).

Kyte and Doolittle, "A Simple Method for Displaying the Hydropathic Character of a Protein," *J. Mol. Biol.* 157, 105–132 (1982).

Landschutz, et al., "The Leucine Zipper: A Hypothetical Structure Common to a New Class of DNA Binding Proteins," *Science* 240, 1759–1764; *Science* 240, 1759–1764 (1988).

Lewis and Dean, "Automated Site–Directed Drug Design: The Formation of Molecular Templates in Primary Structure Generation," *Proc. R. Soc. Lond.* 236, 125–140 and 141–162 (1989).

Lovell–Badge *Tetarocarcinomas and Embryonic Stem Cells, A Practical Approach*, E.J. Robertson, editor (IRL Press 1987) (Table of Contents Only).

McKinley and Rossmann, "Rational Design of Antiviral Agents," *Annu. Rev. Pharmacol. Toxiciol.* 29, 111–122 (1989).

Mel, et al., "A Computational Approach to Mechanism of Self–Cleavage of Hammerhead RNA," *Proc. Natl. Acad. Sci.* 86:9727 (1989).

Messing, et al., "A System for Shotgun DNA Sequencing" *Nucleic Acids Res.* vol. 9, No. 2, pp. 309–321 (1981).

Mirchoff et al., "Delineation of Sodium–Stimulated Amino Acid Transport Pathways in Rabbit Kidney Brush Border Vesicles," *J. Membr. Biol.* 64, 113–122 (1982).

Nadler, "Aspartate and Glutamate as Possible Transmitters of Excitatory Hoppocampal Afferents," *Nature* 260, 538–540 (1987).

Nadler, "Sodium–Dependent Proline Uptake in the Rat Hippocampal Formation: Association with Iosilateral–Commissural Projections of CA3 Pyramidal Cells," *J. Neurochem*, vol. 49, No. 4, pp. 1155–1160 (1987).

Nickolson, "'On' and 'Off' Responses of K+–Induced Synaptosomal Proline Release: Involvement of the Sodium Pump," *J. Neurochem.* 38, 289–292 (1982).

Pacholozyk, et al., "Expression Cloning of a Cocaine–and Antidepressant–Sensitive Human Noradrenaline Transporter," *Nature* 350, 350–354 (1991).

Perry and Davies, "The Use of 3D Modelling Databases for Identifying Structure Activity Relationship," *OSAR: Quantitative Structure–Activity Relationships in Drug Design* pp. 189–193 (Alan R. Liss, Inc. 1989).

Peterson and Raghupathy, "Characteristics of Amino Acid Accumulation by Synaptosomal Particles Isolated from Rat Brain," *J. Neurochem.* 19, 1423–1438 (1972).

Potter, "Enhancer–Dependent Expression of Human K Immunoglobulin Genes Introduced into Mouse Pro–B Lymphocytes by Electroporation," *Proc. Natl. Acad. Sci. USA* 81, 7161 (1984).

Rebek, "Model Studies in Molecular Recognition" *Science* 235, 1478–1481 (1987).

Rebek et al., "Convergent Functional Groups, 3 A Molecular Cleft Recognizes Substrates of Compelmentary Size, Shape, and Funcationality," *J. Am. Chem. Soc.*, 109, 2426–2431 (1987).

Ripka "Computers Picture the Perfect Drug," *New Scientist* 54–57 (Jun. 16, 1988).

Sandri–Goddin, et al., "High–Frequency Transfer of Cloned Herpes Simplex Virus Type 1 Sequences to Mammalian Cells by Protoplast Fusion," *Molec. Cell Biol.* 1, 743 (1981).

Sanger, et al., "DNA Sequencing with Chain–Terminating Inhibitors," *Proc. Natl. Acad. Sci. USA* 74, 5463–5467 (1977).

Schousboe, A., "Transport and Metabolism of Glutamate and Gaba in Neurons and Glial Cells," *Int. Rev. Neurobiol.* 22, 1045 (1981).

Schwartz, E.A., "Depolarization Without Calcium Can Release $\gamma$–Aminobutyric Acid from a Rentinol Neuron," *Science* 238, 350–356 (1987).

Shimada, et al., "Cloning and Expression of a Cocaine–Sensitive Dopamine Transporter Complementary DNA," *Science*, vol. 254, pp. 576–578 (1991).

Snyder, S.H., "Putative Neurotransmitters in the Brain: Selective Neuronal Uptake, Subcellular Localization, and Interactions with Cetrally Acting Drugs," *Biol. Psychiatry* 2, 367–389 (1970).

Snyder S.H. "Vehicles of Inactivation," *Nature* 354, 187 (1991).

Sompayrec et al "Efficient Infection of Monkey Cells with DNA of Simlan Virus 40," *Proc. Natl. Acad. Sci. USA* 78, 7575–7578 (1981).

Southern and Berg, "Transformation of Mammalian Cells to Antibiotic Resistance with a Bacterial Gene Under Control of the SV40 Early Region Promoter," *J. Mol. Appl. Gen.* 1:327–341 (1982).

Stevens, et al. "Amino Acid and Sugar Transport," *Annu. Rev. Physiol.* 46, 417–433 (1984).

Tiedge, "The Use of UV Light as a Cross–Linking Agent for Cells and Tissue Sections in In Situ Hybridization," *DNA And Cell Biology*, vol. 10, No. 2 (Mar. 1991).

Wright and Peerce, "Identification and Conformational Changes of the Intestinal Proline Carrier," *J. Biol. Chem.* 259, 14993–14996 (1984).

Zimmer and Gruss, "Production of Chimaeric Mice Containing Embryonic Stem (ES) Cells Carrying a Homoeobox Hox 1.1 allele Mutated by Homologous Recombination," *Nature* 338, 150–153 (1989).

McCormack et al., "Leucine–Zipper Motif Update," *Nature* 340, 103–104 (1989).

Sambrook, Frisch & Maniatis, *Molecular cloning: A Laboratory Manual*, 2nd Ed (Cold Spring Harbor Laboratory NY 1989) (Table of Contents Only).

Fremeau, et al., "Molecular Cloning and Expression of a High Affinity L–Proline Transporter Expressed in Putative Glutamatergic Pathways of Rat Brain," *Neuron*, 8:915–926 (1992).

Kilty and Amara, "Families of twelve transmembrane domain transporters," *Current Opinion in Biotechnology*, 3:675–682 (1992).

Liu, et al., "A Family of Genes Encoding Neurotransmitter Transporters," *Proc. Natl. Acad. Sci. USA*, 89:6639–6643 (1992).

Snutch, "The use of *Xenopus oocytes* to probe synaptic communication," *TINS*, 11(6):250–256 (1988).

Uhl, et al., "Neurotransmitter Transporter Family cDNAs in a Rat Midbrain Library: 'Orphan Transporters' Suggest Sizable Structural Variations," *Mol. Brain Res.*, 16:253–259 (1992).

Balcar, V. J., et al. (1976) *Brain Res.* 102: 143–51.

```
            ┌─────────────────8─────────────────┐                          ┌─────9─────┐
rPROT  SVLGYHSQELGVPVDQVAKA.GPGLAFVIYPQAMTHLPLSPPNSFLTTMLLTLGLDSQPAFLETIVIAVTDEFPYYLRPKKAVPSGLICVAMY.LMGLI  rPROT
rGAT1  SIVGFMAHVTKRSIADVAAS.GPGLAFLAYPEAVTQLPISPLNAILTTSMLLALGIDSQPCTVEGFITALVDEYPRLLRNRRELFIAAVCIVSY.LIGLS  rGAT1
hNET   SILGYHAEHKVNIEDVATE.GAGLVFILYPEAISTLSGSTMAVVFVMLLALGLDSSMGGMEAVITGLADDFQVLKRHRK.LFTTGVTFSTF.LLALF  hNET
rSERT  TVLGYMAERNRNEDVSEVAKDAGPSLLFITYAEAIANMPASTFFAIIFPLKLITLGLDSTPAGLEGVITAVLDEFP.HIWAKRREWFVLIVITCVLGSLL  rSERT
rDAT   SFLGYHAQKHNVPIRDVATD.GPGLIFIIYPEAIATLPLSSAMAAVTFLMLLTLGIDSAMGGMESVITGLVDEFQ.LLHRHRELFTLGIVLATF.LLSLF  rDAT
                       ┌───────────10───────────┐                      ┌──────────11──────────┐

┌──────────────12──────────────┐
rPROT  LTTDGGMYWLVLLDDYSAS.PGLMVVITTCLAVTRVYGIQRFCRDIHMMLGFKPGLYF.RACWLTLSPATLLALLVYSIVKYQPSEYGS.YRFPAWAEL  rPROT
rGAT1  NITQGGIYVFKLFDYYSASGHSLLFLVFPECVSISWFYGVNRFYDNIQEHVGSRPCIW.WRLCMSPFTPIIVAGVTLFSAVQMTPLTMGS.YVFPKWGQG  rGAT1
hNET   CITKGGIYVLTLLDTPAAGTSILFA.VLMEAIGVSWFYGVDRFSNDIQQMMGFRPGLY.WRLCWKFVSPAFLLFVVVSIINFKPLTYDD.YIFPPWANW  hNET
rSERT  TLTSGGAYVVTLLEEYATGPAVLTV.ALIEAVAVSWFYGITQFCSDVTEKRLGFSPGWF.WRICWVAISPLFLF.IICSFLMSPPQLRLFQINYPHWSIV  rSERT
rDAT   CVTNGGIYVFTLLDHFPAAGTSILFG.VLIEAIGVANFYGVQQFSDDIKQMTGQRPNLY.WRLCWLVSPCFLLYVVVSIVTFRPPHYGA.YIFPDWANA  rDAT rPROT  LGILMGLLSCLM.IPAGHLVAVLRBEGSLWERLQQASRPAIDMGPSLEEN.RTGMYVATLAGSQSPKPLMVHMRKYGGITSFENTAIEVDRETAEEEES  rPROT
rGAT1  VGWLMALSSHVL.IPGYMAYMFLTLKGSLKQRLQVMIQPSEDIVRPENGPE.....QPQAGSSASKEAYI................  rGAT1
hNET   VGWGIALSSHVL.VPIYVIYKFLSTQGSLWERLAYGITPEMEHHLVAQRDIRQFQLQHMLAI..................  hNET
rSERT  LGYCIGMSS.VICIPTYIIYRLIST.PGTLKERIIKSITPETPTEIPCG.DIRMNAV....................  rSERT
rDAT   LGWIIATSSMAM.VPIYATYKFCSLPGSFREKLAYAITPEKDHQLVDRGEVRQFTLRHMLLL.................  rDAT
```

HIGH AFFINITY L-PROLINE TRANSPORTER POLYPEPTIDES; ANTIBODIES AND IMMUNOASSAYS SPECIFIC FOR THEM

This application is a divisional of U.S. Ser. No. 07/879,617 filed on May 1, 1992, by Robert T. Fremeau, Jr., Marc G. Caron, and Randy D. Blakely entitled "High Affinity, Brain-Specific Nucleic Acids Encoding a L-Proline Transporter, and Vectors, and Host Cells Comprising the Same," now U.S. Pat. No. 5,580,775.

The United States government has rights in this invention by virtue of National Institutes of Health grants NS 19576, 2P50-MH 40159, and IP-53-NIH 44211 to M.G.C., and NIDA DA07390-01.

BACKGROUND OF THE INVENTION

Rapid chemical signaling between neurons and target cells is dependent upon the precise control of the magnitude and duration of action of neurotransmitters in synaptic spaces. Two principal mechanisms are responsible for rapid transmitter inactivation. Either the neurotransmitter can be enzymatically metabolized to an inactive product, as with the hydrolysis of acetylcholine by acetylcholinesterase, or the neurotransmitter can be actively transported back into presynaptic nerve terminals or surrounding glial cells by one of a large number of specific, pharmacologically distinguishable membrane transport proteins, as reviewed by Snyder, 1970 *Biol. Psychiatry* 2, 367–389.

Presynaptic nerve endings are enriched for transporters specific to the neurotransmitter they release, thus ensuring constant high levels of neurotransmitters in the nerve terminals, as well as low concentrations in synaptic spaces.

Active transport of neurotransmitters across plasma membranes is energetically coupled to the transmembrane $Na^+$ gradient generated by $(Na^+,K^+)$ATPase. Additional ions, including intracellular $K^+$ and extracellular $Cl^-$, are also required for transport of many neurotransmitters. Ion sensitivities of neurotransmitter transporters appear to reflect their cotransport with the neurotransmitter during each translocation cycle. These energetic properties, along with clear pharmacological differences, differentiate the $Na^+$-dependent plasma membrane transporters from the intracellular, $(H^+)$ATPase-coupled vesicular transporters that concentrate neurotransmitters in synaptic vesicles for exocytosis. Although glial cells express $Na^+$-dependent neurotransmitter transporters, as reported by Schousboe, A. (1981) *Int. Rev. Neurobiol.* 22, 1045, the quantitative contribution of glial carriers to synaptic transmission is poorly understood. $Na^+$-dependent transport processes also mediate the presynaptic accumulation of certain substrates for neurotransmitter synthesis. For example, the rate-limiting step in the biosynthesis of acetylcholine appears to be $Na^+$-dependent choline uptake into cholinergic nerve terminals (Kuhar and Murrin, (1978) *J. Neurochem.* 30, 15–21). It has been proposed that during depolarization, physiologically relevant $Ca^{2+}$-independent release of neurotransmitters may occur by reversal of the $Na^+$-dependent uptake process (Schwartz, E. A. (1987) *Science* 238, 350–355).

High affinity, $Na^+$-dependent uptake activities, analogous to the noradrenergic carrier first described at peripheral synapses, have been identified in the mammalian central nervous system (CNS) nerve terminals for the biogenic amine neurotransmitters, including norepinephrine (NE), dopamine (DA), and serotonin (5HT), as reviewed by Snyder, S. H. (1991) *Nature* 354, 187. The association of high affinity, $Na^+$-dependent transport mechanisms in specific neural pathways in the mammalian CNS has provided important information toward the identification of amino acid neurotransmitter candidates. Thus, high affinity, $Na^+$-dependent uptake activities have been identified in synaptosomes and brain slices for the excitatory amino acids L-glutamate and L-aspartate and the inhibitory amino acids gamma-aminobutyric acid (GABA) and glycine. Presumably, these uptake activities contribute to the regulation of synaptic levels of the transmitter amino acids.

High affinity, $Na^+$-dependent uptake of L-proline has also been described in rat brain synaptosomes and slices, as reported by Bennett, et al., (1972) *Science* 178, 997–999, Peterson and Raghupathy, (1972) *J. Neurochem.* 19, 1423–1438, Balcar, et al., (1976) *Brain Res.* 102, 143–151, Hauptman, et al., (1983) *FEBS Lett.* 161, 301–305, and Nadler, (1987) *Nature.* 260, 538–540. Furthermore, like the well-established neurotransmitter amino acids, exogenously loaded radiolabeled L-proline is released from brain slices and synaptosomes in a $Ca^{2+}$-dependent manner following $K^+$-induced depolarization, as reported by Bennett et al., (1974) *Life Sci.* 75, 1045–1056; Balcar et al., (1976) *Brain Res.* 102, 143–151; and Nickolson, (1982) *J. Neurochem.* 38, 289–292.

In contrast, numerous other amino acids that are not thought to have neurotransmitter roles lack high affinity, $Na^+$-dependent synaptosomal uptake activities and are not released to a significant extent from brain slices by $K^+$-induced depolarization (Bennett et al., 1974).

The recent cloning and molecular characterization of specific $Na^+$-dependent membrane transport proteins for GABA and NE established the presence of a distinct gene family of neurotransmitter transport proteins. These transporters possess significant, greater than 46%, but dispersed amino acid sequence identities and exhibit similar inferred topographies. Both transporters are composed of polypeptides of approximately 600 amino acids and contain approximately 12 hydrophobic stretches of 18–25 amino acids that are thought to form transmembrane domains, analogous to findings with other membrane transport proteins. Amino acid sequence conservation among pharmacologically distinct neurotransmitter transporters likely reflects the involvement of these regions in common transport functions, such as the maintenance of transporter topology and/or the coupling of substrate translocation to the transmembrane $Na^+$ gradient. However, no significant sequence similarity is observed with other membrane transport proteins, including the mammalian facilitated glucose carriers, the mammalian $Na^+$/glucose cotransporter, the prokaryotic $Na^+$-dependent cotransporters, and the ATP-binding cassette membrane transporters, including the multidrug resistance P glycoproteins and the cystic fibrosis transmembrane conductance regulator.

Recently, cDNA clones have been identified that encode rat brain DA by Giros et al., (1991) *FEBS Lett.* 295, 149–154; Kilty, et al., (1991) *Science* 254, 78–79; and Shimada et al., (1991) *Science* 254, 576–578, and 5HT by Blakely et al., (1991) *Nature* 354, 66–70; Hoffman et al., (1991) *Science* 254, 579–580, transporters. These sequences facilitate further study of the transporters they encode and have potential as diagnostic agents.

It is therefore an object of the present invention to provide a nucleic acid sequence encoding a high affinity, $Na^+$-dependent rat brain L-proline transporter.

It is a further object of the present invention to provide probes for related transporter molecules and for studying function and disorders involving these transporter molecules.

SUMMARY OF THE INVENTION

The anatomical distribution, pharmacological properties, and structural features of a cDNA encoding a high affinity, $Na^+$-dependent rat brain L-proline transporter is described. The expression of this carrier in subpopulations of putative glutamatergic pathways supports a specific role for L-proline in excitatory amino acid neurotransmission.

The polymerase chain reaction (PCR) was used with degenerate oligonucleotides derived from two conserved regions of the norepinephrine and gamma-aminobutyric acid transporters to identify $Na^+$-dependent transporters in rat brain. One PCR product hybridized to a 4.0 kb RNA concentrated in subpopulations of putative glutamatergic neurons including mitral cells of the olfactory bulb, pyramidal cells of layer V of the cerebral cortex, pyramidal cells of the piriform cortex, and pyramidal cells of field CA3 of the hippocampus. Transient expression of the cognate cDNA conferred $Na^+$-dependent L-proline uptake in HeLa cells that was saturable ($K_m$=9.7 µM) and exhibited a pharmacological profile similar to that for high affinity L-proline transport in rat brain slices. The cloned transporter cDNA predicts a 637 amino acid protein with 12 putative transmembrane domains and exhibits 44%–45% amino acid sequence identity with other neurotransmitter transporters. These findings support a synaptic role for L-proline in specific excitatory pathways in the CNS.

The sequence can be used for expression of the transporter molecule in host cells that do not normally express the protein, to make nucleic acid and antibody probes for the same protein from other species and related proteins, in diagnostic assays, and to design functional and structural analogs for use in research and possible clinical treatments. The protein is useful in making antibodies, research studies, and design of modulating compounds for clinical treatments.

BRIEF DESCRIPTION OF THE DRAWINGS

(FIG. 1A) Northern blot analysis. Autoradiograph (1 week) of hybridization of an rTB2-2 cDNA probe to a nylon transfer of total RNAs (20 µg) derived from the indicated rat tissues and rat and human cell lines. A 4.0 kb hybridizing RNA was detected in discrete regions of the rat brain. No specific hybridizing bands were detected in rat adrenal gland or in rat pheochromocytoma (PC12) cells, rat CA-66 medullary thyroid carcinoma cells, human SK-N-SH cells, or human HeLa fibroblasts. Sizes are in kilobases and were determined using RNA standards (Bethesda Research Laboratories).

(FIGS. 1B–E) In situ hybridization. Horizontal (B), coronal (C), and sagittal (D) sections of adult rat brain were hybridized with $^{35}S$-labeled antisense RNA derived from PCR fragment rTB2-2. The horizontal section in (E) was taken adjacent to the section displayed in (B) but was hybridized with a $^{35}S$-labeled sense-strand control probe. Abbreviations: CA3, pyramidal cell layer of field CA3 of Ammon's horn; CPu, caudate-putamen; Ent, entorhinal cortex; Mi, mitral cell layer of the olfactory bulb; Pir, piriform cortex; Thal, thalamus; V, layer V of the cerebral cortex; VI, layer VI of the cerebral cortex.

FIGS. 2A-1 and 2A-2 are an alignment of deduced amino acid sequences encoding rat proline, rat GABA, human norepinephrine, rat serotonin, and rat dopamine transporters. Amino acid sequence alignments were produced by iterative use of the BESTFIT routine of the Wisconsin GCG software package. Shaded regions represent sequences absolutely conserved across all five transporters. Solid lines above rPROT reflect location of 12 proposed transmembrane domains. Asterisks denote residues defining the conserved leucine zipper motif. Abbreviations; rPROT, rat proline transporter (SEQ ID NO: 8); rGAT1, rat GABA transporter (SEQ ID NO: 10); hNET, human norepinephrine transporter (SEQ ID NO: 11); rSERT, rat serotonin transporter (SEQ ID NO: 12); rDAT, rat dopamine transporter (SEQ ID NO: 13).

FIG. 3A is a graph of the time course of L-[$^3$H]proline accumulation into HeLa cells transfected with pPROT. $Na^+$ dependence was examined by isotonic substitution of assay NaCl with choline chloride. Background levels of proline transport were determined by transfecting HeLa cells under identical conditions with pBluescript SKII(–). Data represent the mean±SEM of triplicate determinations. The symbol ■ represents cells transfected with pPROT in the presence of NaCl. The symbol ▲ represents cells transfected with pBluescript in the presence of NaCl. The open square symbol represents cells transfected with pPRPT in the presence of choline chloride.

FIG. 3B is a graph of the uptake velocity of 50 nM L-($^3$H)proline determined in the presence of increasing concentrations of unlabeled L-proline during a 20 min. incubation in transfected HeLa cells. Data represent the mean±SEM of three separate experiments each done in triplicate. FIG. 3C depicts an Eadie-Hofstee analysis of initial velocity data.

DETAILED DESCRIPTION OF THE INVENTION

Figure 1A:
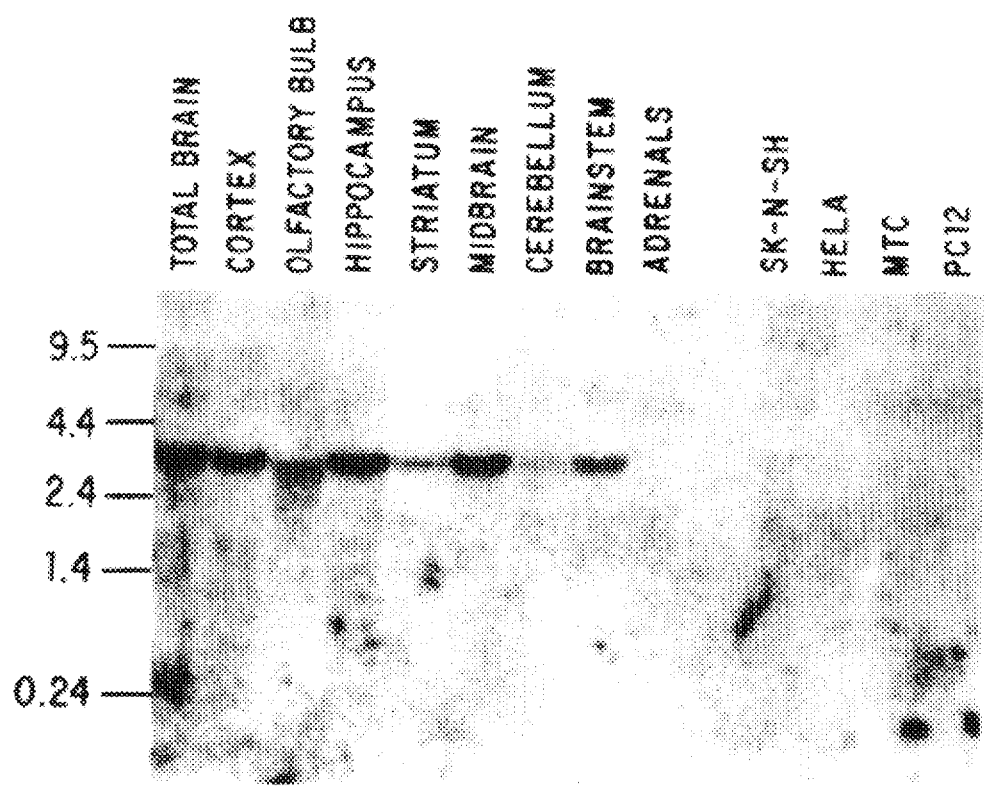
FIGS. 1A–E. Northern Blot and in Situ Localization of RNA Hybridizing to PCR Clone rTB2-2.

The following studies were conducted to determine the anatomical distribution, pharmacological properties, and structural features of a cDNA encoding a high affinity, $Na^+$-dependent rat brain L-proline transporter.

Isolation of Neurotransmitter Transporter Sequences from Rat Brain by PCR Using Degenerate Oligonucleotide Primers.

To identify previously undetected neurotransmitter transporter proteins expressed in mammalian brain, synthetic degenerate oligonucleotide primers derived from conserved amino acid sequences from the first and sixth transmembrane domains (SEQ ID NOs: 1 and 2, respectively) of the human NE and rat GABA transporters were synthesized and utilized for PCR amplification of rat brain cDNA. Reaction products of approximately 700 bp were purified, subcloned, and sequenced.

Synthetic, degenerate oligonucleotides shown in the Sequence Listing as SEQ ID NOs: 3 and 4, respectively, were designed to encode two highly conserved amino acid stretches near the first (SEQ ID NO: 1) and sixth (SEQ ID NO: 2) transmembrane domains, respectively, of the human NE (Pacholczyk et al., 1991) and rat GABA (Guastella et al., 1990) transporters. Residues 1–9 in SEQ ID NO: 3 and residues 1–9 in SEQ ID NO: 4 represent addition of 5' restriction sites for cloning. Single-stranded rat brain cDNA was synthesized from poly(A)+ RNA with random hexamer primers as described by the manufacturer (Amersham). Oligonucleotides were combined with single-stranded rat brain cDNA into PCRs conducted with Taq polymerase as described by the manufacturing (Promega) for 30 cycles of 94° C. for 1 minute, 45° C. for 2 minutes, 72° C. for 3 minutes, with a final extension of 15 minutes. Products of approximately 700 bp, after phenol extraction and ethanol precipitation, were digested with EcoRi to prevent recloning the rat GABA transporter (Guastella et al., 1990), which has an EcoRI restriction site between the oligonucleotides used for amplification, and digested with XbaI and XhoI to produce staggered ends for cloning.

Samples were gel purified (Gene Clean, Bio 101), and ligated into XbaI- and XhoI-digested pBluescript SKII(−) (Stratagene).

Partial sequencing of PCR product rTB2-2 was achieved by dideoxynucleotide chain termination using Sequence (USB).

To isolate a full-length cDNA clone, cDNA from PCR fragment rTB2-2 was used as a template for the synthesis of a 186 bp PCR probe using a 5' sense-strand oligonucleotide of the sequence shown as SEQ ID NO: 5 and a 3' antisense oligonucleotide of the sequence shown as SEQ ID NO: 6 oligonucleotides were combined with rTB2-2 template DNA (18 ng) into a PCR in the presence of 400 µCi of [$^{32}$P]dCTP (3000 Ci/mmol) and amplified with Taq polymerase as described by the manufacturer (Perkin Elmer) for 30 cycles of 94° C. for 1 minute, 55° C. for 1 minute, 72° C. for 2 minutes, with a final extension time of 8 minutes. The $^{32}$P-labeled PCR probe was used to screen $1\times10^6$ phage recombinants from a rat forebrain cDNA library in lambda Zap II (Stratagene). Duplicate nylon filters (Biotrans Membranes, Inc.) were hybridized at 42° C. in a buffer containing 5×SSC (1×SSC=0.15M NaCl, 0.015M sodium citrate [pH 7.0]), 5×Denhardt's solution, 0.05M sodium phosphate (pH 6.5), 0.1% SDS, 50% formamide, 200 µg/ml sheared salmon sperm DNA, and $6.2\times10^6$ cpm/ml $^{32}$P-labeled PCR probe. After hybridization, filters were washed for 30 minutes at room temperature (twice) in 1×SSC, 0.1% SDS. The filters were then washed for 15 minutes at 65° C. (twice) in 0.2×SSC, 0.1% SDS. Bluescript plasmids (pB5 SKII(−)) were rescued from plaque-purified positive rTB2-2 cDNA clones by in vivo excision as described by the manufacturer (Stratagene).

The nucleotide sequence was determined on both strands from alkaline lysate minipreps of double-stranded DNA by dideoxynucleotide chain termination using Sequenase. Nucleotide sequences were assembled using Wisconsin GCG programs. Deduced amino acid sequences of rTB2-2-20 were compared with protein sequences translated from nucleotide sequences stored in the GenBank and EMBL data bases. The extent of protein sequence similarity was calculated as described by Dayhoff et al. (1983).

One PCR-derived sequence, rTB2-2, displayed a similar identity in its deduced amino acid sequence (61%–65%) with the previously cloned amino acid (GABA) and biogenic amine (DA, NE, and 5HT) transporters. Because rTB2-2 did not display any greater similarity with the amino acid or the biogenic amine transporters, no initial clues as to the substrate class of this putative transporter could be determined. To gain insights into the possible substrate for this potential transporter, the size and regional distribution of RNA transcripts that hybridize to rTB2-2 in the rodent brain were determined.

rTB2-2 is Encoded by a 4.0 kb mRNA Expressed in Excitatory Pathways in Rat Brain.

cDNA derived from PCR fragment rTB2-2 (100 ng) was radiolabeled with $^{32}$P-labeled dCTP (50 µCi) using random oligodeoxynucleotide primers (Amersham) and hybridized to a nylon (Zetaprobe, Bio-Rad) transfer of total RNAs (20 µg) derived from rat tissues and rat and human cell lines. The blot was prehybridized at 42° C. in 50% formamide, 5×SSPE (1×SSPE–150 nM NaCl, 10 mM NaH$_2$PO$_4$ [pH 7.4], 1 mM EDTA [pH 8.0]), 5×Denhardt's solution, 10% dextran sulphate, 1% SDS, 100 µg/ml salmon sperm DNA for 2 hours. Probe was added, and hybridization was continued for 14 hours. The blot was rinsed with two 20 minute washes in 2×SSPE, 0.1% SDS (22° C.), followed by a 1 hour rinse at 65° C. in 0.1×SSPE, 0.1% SDS, and then exposed to autoradiographic film with an intensifying screen for 5 days. All lanes were equivalently loaded based on even intensity of ribosomal RNAs. The foregoing conditions are defined herein as standard hybridization conditions.

In situ hybridization was conducted on 4% paraformaldehyde-postfixed adult rat brain sections as previously described (Fremeau and Popko, 1990). Briefly, male Sprague-Dawley rats (300–375 g; Charles River Breeding Laboratories) were killed by decapitation. Brains were removed and frozen on an aluminum block cooled with liquid nitrogen. Frozen sections (10 µm) in the coronal, sagittal, and horizontal planes were prepared in a cryostat, mounted onto room temperature slides (Onasco Biotech, Houston, Tex.) and stored at −70° C. until processed for in situ hybridization. Synthetic [$^{35}$S]UTP-labeled single-stranded RNA was synthesized with the 710 bp PCR fragment rTB2-2, by in vitro transcription from the T3 promoter after plasmid linearization with XhoI (antisense orientation) or from the T7 promoter after linearization with XbaI (sense orientation). Tissue sections were thawed and fixed for 10 minutes in 4% paraformaldehyde in phosphate-buffered saline at 4° C. The sections were rinsed in 2×SSC, covered with a minimal volume of 2×SSC, and illuminated with a germicidal ultraviolet lamp (30 W, wide spectrum ultraviolet light) for 5 minutes at a distance of 30 cm in accordance with the method of Tiedge et al., DNA Cell Biol. 10:143–147 (1991). The sections were then rinsed in 2×SSC, covered with prehybridization buffer (50% formamide, 0.6M NaCl, 10 mM Tris-HCl[pH 7.5], 0.02% Ficoll, 0.02% polyvinyl pyrollidone, 0.1% bovine serum albumin, 1 mM EDTA [pH 8.0], 50 µg/ml salmon sperm DNA, 500 µg/ml yeast total RNA, 50 µg/ml yeast tRNA), and stored at 50° C. for 1 hour. Prehybridization buffer was removed, and the slides were covered with hybridization buffer (50% formamide, 0.6 M NaCl, 10 mM Tris-HCl (pH 7.5) 0.02% Ficoll, 0.02% polyvinyl pyrollidone, 0.1% bovine serum albumin, 1 mM EDTA [pH 8.0], 10 µg/ml salmon sperm DNA, 50 µg/ml yeast total RNA, 50 µg/ml yeast tRNA, 10 mM dithiothreitol, 10% dextran sulphate) containing $^{35}$S-labeled probes (2.5–5.0×10$^6$ cpm/ml; heat-denatured for 15 minutes at 65° C.). Hybridization was performed for 16–18 hours at 50° C. Following hybridization, the sections were washed for 60 minutes in 2×SSC at 50° C. and then treated with RNAase A (50 µg/ml) for 60 minutes at 37° C. The sections were then washed in 2×SSC for 60 minutes at 50° C., followed by a final high stringency wash in 0.1×SSC, 14 mM β-mercaptoethanol, 0.15% sodium pyrophosphate for 3

FIG. 1A demonstrates that PCR product rTB2-2 hybridizes to a single 4.0 kb RNA present in multiple regions of rat brain. The strongest hybridization signals are observed in cerebral cortex, hippocampus, and midbrain. Intermediate signals are observed in the olfactory bulb and brain stem, while only weak hybridization is observed in the striatum (caudate-putamen) and cerebellum. No specific hybridizing species were detected in rat adrenal glands or the human SK-N-SH, human HeLa, rat medullary thyroid carcinoma, and rat PC12 cell lines, indicating that PCR fragment rTB2-2 does not represent a ubiquitous transporter that might subserve a general metabolic role.

Figure 1B:
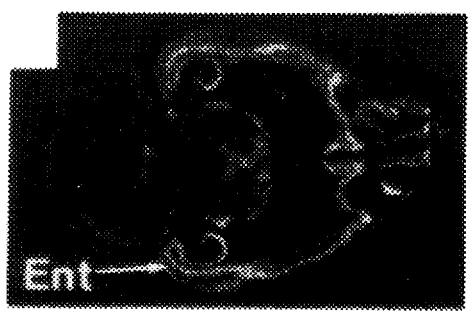
Figure 1C:
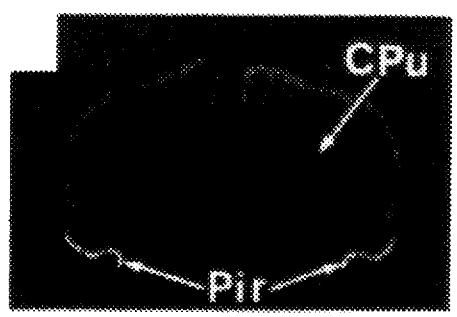
Figure 1D:
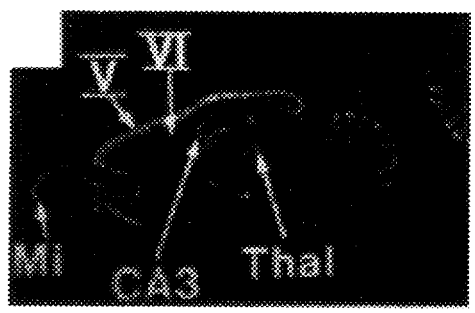
Figure 1E:

To identify more clearly the cellular localization of RNAs hybridizing to PCR product rTB2-2, 4% paraformaldehyde-fixed rat brain sections were hybridized with $^{35}$S-labeled antisense RNA derived from PCR fragment rTB2-2. FIGS. 1B–1D reveal that rTB2-2 mRNA is heterogeneously expressed in adult rat brain. Prominent hybridization signals were observed over subpopulations of putative glutamatergic neurons, including mitral cells of the olfactory bulb, pyramidal cells of layer V of the cerebral cortex, pyramidal cells of the piriform cortex, and the entorhinal cortex. Furthermore, labeled cells were also observed in layer VI of the cerebral cortex, particularly the pericallosal region at all layers examined. Labeled cells were also observed scattered throughout the cerebral cortex. Within the hippocampus, rTB2-2 mRNA was heterogeneously distributed. Prominent hybridization signals were observed over the CA3 pyramidal cells, and moderate labeling was seen over the CA1 pyramidal cells, whereas little or no specific labeling was observed over the granule cells of the dentate gyrus. Moderate hybridization signals were detected over the midbrain, thalamus, hypothalamus, and brain stem. Within the cerebellum, the granule cell layer exhibited specific though less consistent hybridization (FIGS. 1B and 1D). Little or no specific labeling was observed over the caudate-putamen, white matter tracts, choroid plexus, ependymal cells of the cerebral ventricles (FIGS. 1B–1D), or sections hybridized with a sense-strand control probe (FIG. 1E).

Characterization of rTB2-2 cDNAs.

PCR fragment rTB2-2 was used to isolate cDNA clones from a rat forebrain cDNA library, described by Hollman, et al., *Nature* 342, 643–645 (1989). Several candidate clones were obtained, two of which contained the entire coding region of a single 1911 bp open reading frame within which was found the sequence of PCR fragment rTB2-2. The nucleotide and deduced amino acid sequences of clone rTB2-2-20 are shown in the Sequence Listing as SEQ ID NOS: 7 and 8, respectively.

The first ATG (residues 91–93) present in the cDNA was assigned as the initiation codon on the basis that it conformed to the translation initiation consensus sequence of Kozak *Nucl. Acids. Res.* 15, 8125–8148 (1987); and because the proposed translation initiation codon is 39 bp downstream from a single in-frame stop codon.

Nucleotide and Deduced Amino Acid Sequences of rTB2-2-20.

Nucleotides are numbered in the 5' to 3' direction beginning with the first residue of the codon for the putative initiator methionine. The nucleotides on the 5' side of amino acid residue 1 are indicated by negative numbers. The stop codon flanking the open reading frame in the amino acid sequence follows Met667 (SEQ ID NO: 8). Twelve putative membrane-spanning domains occur at amino acid residues Phe76-Tyr95; Gly103-Leu123; Gly147-Ile167; Leu247-Val266; Val272-Leu294; Ala321-Ser341; Thr353-Leu375; Ala404-Leu427; Ala454-Thr473; Ser487-Gly508; Ala530-Val549; Leu567-Leu589. The precise locations of the borders of the transmembrane domains are arbitrary and are drawn for convenience of representation. One potential N-linked glycosylation site located on the large putative extracellular loop connecting transmembrane domains 3 and 4 occurs at Asn212-Leu213. Two additional putative glycosylation sites are located, one each, within the putative intracellular N- and C-terminal domains. One putative intracellular consensus sequence for cAMP-dependent protein kinase phosphorylation Thr71-Gly72, and three putative intracellular consensus sequences for protein kinase C phosphorylation occur at Thr44-Pro45, Ser269-Gly270, and Ser630-Pro631. The remaining two protein kinase A sites and three protein kinase C sites are located in the putative extracellular domains or within the putative transmembrane domains. A polyadenylation signal in the 3' untranslated domain is underlined. A motif resembling a leucine zipper occurs at Leu106–Leu127. PCR fragment rTB2-2 begins at the 5' end with adenine-175 and extends until the 3' end at 884.

The Hydropathy Plot of the Deduced Amino Acid Sequence.

Hydropathy was determined by the method of Kyte and Doolittle *J. Mol. Biol.* 157, 105–132 (1982), with a window size of 19.

The deduced protein sequence (SEQ ID NO: 8) predicts a putative protein of 637 amino acid residues with a molecular mass of the primary translation product of 71 kd. Hydropathy analysis of the putative protein reveals the presence of 12 regions of significantly extended hydrophobicity suitable for the formation of transmembrane domains. The N-terminus does not contain a readily identifiable signal sequence, suggesting that the N-terminus resides on the cytoplasmic face of the membrane, as modeled previously for the rat GABA transporter (Guastella et al., 1990). One canonical site for N-linked glycosylation is present on a large hydrophilic domain present between putative transmembrane domains 3 and 4, in a location similar to that observed for a predicted extracellular loop in the other cloned neurotransmitter transporters. One consensus site for cAMP-dependent protein kinase phosphorylation (Kennelly and Krebs, *J. Biol. Chem.* 266, 13335–15558 (1991)), Thr-14, is present in the N-terminus. Three consensus sites for protein kinase C-dependent protein kinase phosphorylation (Kennelly and Krebs, 1991) are present: one each in the N-terminus (Thr-41) and C-terminus (Ser-600) and one in the putative intracellular loop between transmembrane domains 4 and 5 (Ser-239).

A leucine zipper motif, consisting of 4 leucine residues repeated every seventh amino acid residue, is present in the second putative transmembrane domain. This motif was originally proposed to mediate the dimerization of some DNA-binding protein by Landschutz, et al., (1988) *Science* 240, 1759–1764; *Science* 240, 1759–1764. The leucine zipper motif has also been described in membrane proteins including voltage-gated $K^+$ channels (McCormack et al., (1989) *Nature* 340, 103–104) and glucose transporters (White and Weber, (1989) *Nature* 340, 103– 104), where it may mediate subunit oligomerization in the membrane. This motif is largely conserved across all of the cloned neurotransmitter transporters.

A comparison of the predicted amino acid sequence of rTB2-2-20 with those of cloned neurotransmitter transporters reveals striking amino acid sequence conservation, as demonstrated by FIGS. 2A1-2. The predicted protein encoded by rTB2-2-20 shows 44%–45% amino acid identity and 65%–68% similarity with the rat GABA (Guastella et al., 1990), human NE (Pacholczyk et al., (1991) *Nature* 350, 350–354), rat DA (Giros et al., 1991; Kilty et al., 1991; Shimada et al., 1991), and rat 5HT (Blakely et al., 1991a; Hoffman et al., 1991) transporters. Specifically, 148 amino acids are absolutely conserved among the various cloned neurotransmitter transporters. Many of these residues are within or adjacent to the presumed transmembrane domains.

These results indicate that cDNA clone rTB2-2-20 represents a novel member of the emerging family of neurotransmitter transporters.

Expression of rTB2-2-20 in HeLa Cells Confers High Affinity, $Na^+$-Dependent L-Proline Uptake.

To examine the substrate specificity of the encoded transporter candidate, the 2.2 kb BamHI-XbaI fragment of rTB2-2-20 was subcloned in the sense orientation downstream of the T7 promoter sequence of pCDNA1 (Invitrogen), and the cDNA was transiently expressed in HeLa cells by a T7 vaccinia virus transient expression system (Fuerst et al., (1986) *Proc. Natl. Acad. Sci.* USA 83, 8122–8126; Blakely et al., 1991b).

A BamHl-XbaI fragment of rTB2-2-20 containing the entire coding sequence was cloned in the sense orientation downstream of the T7 promoter of pcDNA-1 (Invitrogen) (designated pPROT). Hela cells, 100–250,000 per well in 24 well plates, were infected with recombinant vaccinia virus strain VTF7-3 (10 pfu per cell), expressing T7 RNA polymerase (Fuerst et al., 1986), followed 30 min. later by liposome-mediated (3 µg per well; Lipotectin, BRL) transfection of pPROT (1 µg per well). L-Proline transport assays were conducted 8–9 hr. after transfection with L($^3$H)proline (50 nM, Dupont, New England Nuclear) as substrate in Krebs-Ringer-Tris-HEPES uptake medium as described (Blakely et al., 1991b). Assays were terminated and washed with ice-cold Krebs-Ringer-Tris-HEPES uptake medium, cells were solubilized with 500 µl of 1% SDS, and accumulated radioactivity was determined by scintillation counting. Triplicate control transfections of pBluescript SKII(–) done under identical conditions were included on each 24 well plate to determine nonspecific transport values, which were subtracted from signals obtained with pPROT. The $Na^+$ dependence of L-[$^3$H]proline uptake was determined by isotonic substitution of assay NaCl with choline chloride. To examine the pharmacological specificity of the cloned L-proline transporter, transport assays were conducted for 20 min. with or without the indicated concentrations of selected pharmacological agents added just prior to the addition of L[$^3$H]-proline.

Figure 3A:
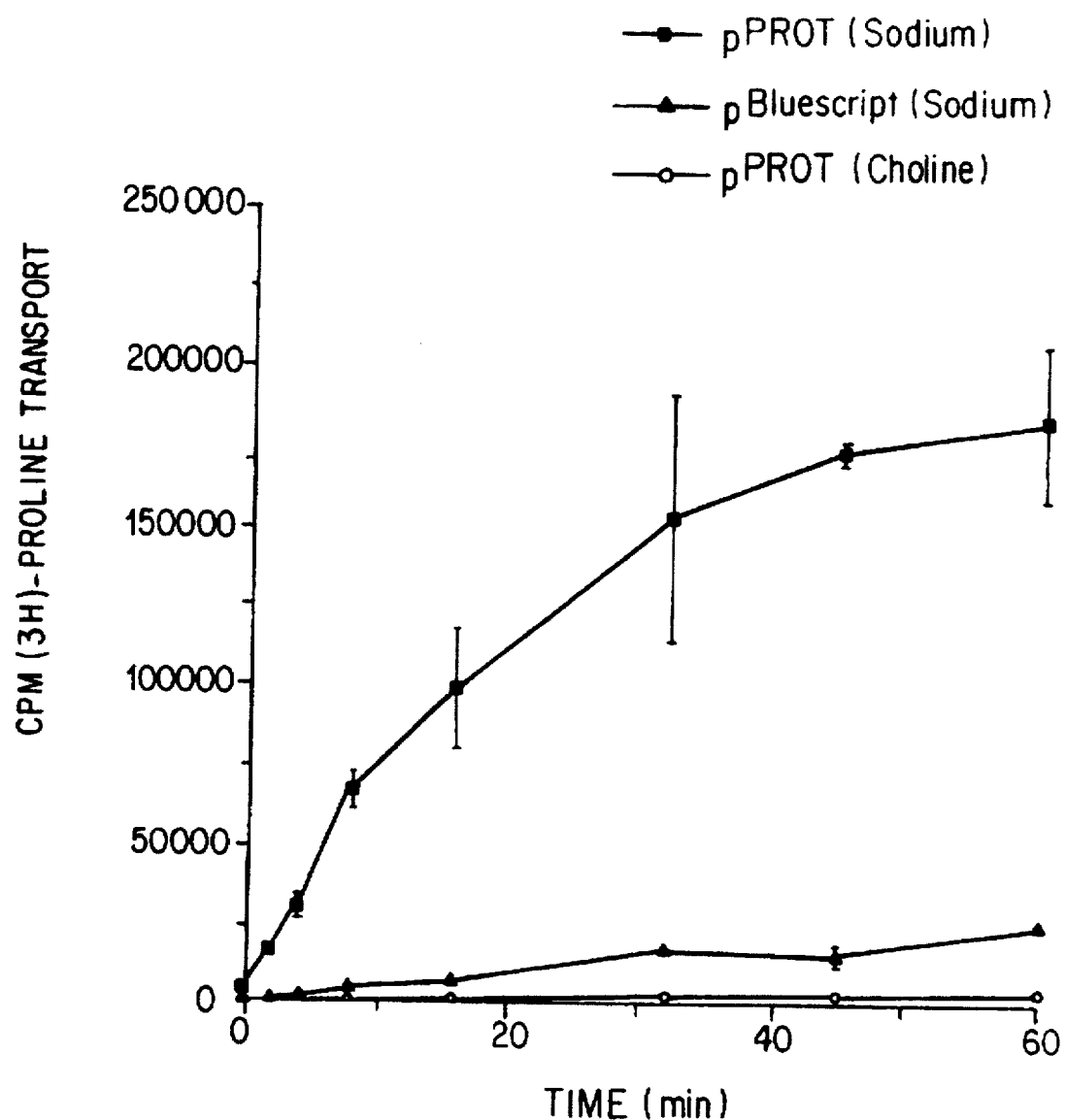
FIGS. 3A–3C show the $Na^+$, Time, and Concentration Dependence of L-Proline Uptake in HeLa Cells Transfected with pROT.
Figure 3B:
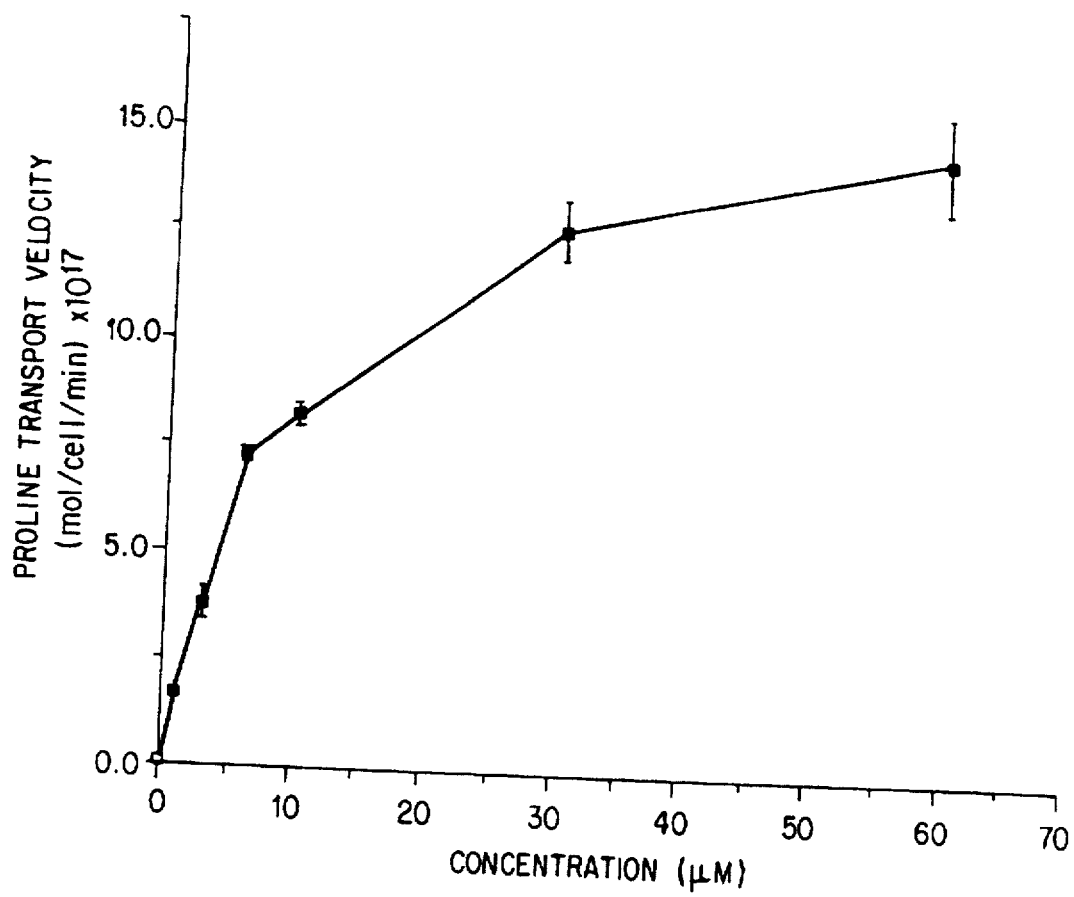
Figure 3C:
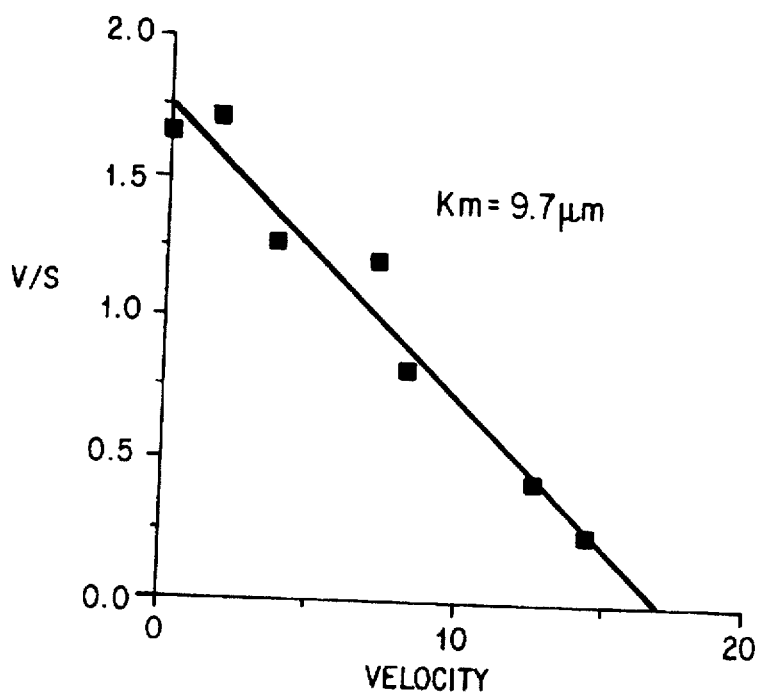

Despite the apparent localization of rTB2-2-20 mRNA in subpopulations of putative glutamatergic cell bodies, transient expression of the novel transporter cDNA did not induce transport of L-[$^3$H]glutamate or D-[$^3$H]aspartate in HeLa fibroblasts, indicating that this clone does not code for an acidic amino acid transporter. However, FIG. 3A demonstrates that HeLa cells transiently transfected with this construct (designated pPROT) express time- and $Na^+$-dependent L-proline uptake. Isotonic substitution of assay NaCl with choline chloride abolished specific L-proline uptake (FIG. 3A). Furthermore, L-proline transport was saturable at low substrate concentrations, exhibiting an apparent Michaelis constant ($K_m$) of 9.7 µM (FIG. 3B).

These results indicate that this cDNA encodes a high affinity $Na^+$-dependent rat brain L-proline transporter. Control experiments conducted with plasmid vector-transfected HeLa cells revealed that endogenous L-proline transport, which was less than 10% of pPROT-induced transport, was $Na^+$-dependent (FIG. 3A), and predominantly of low affinity, with a $K_m$ greater than 200 µM.

Pharmacological Specificity of High Affinity L-Proline Transporter.

Figure 4:
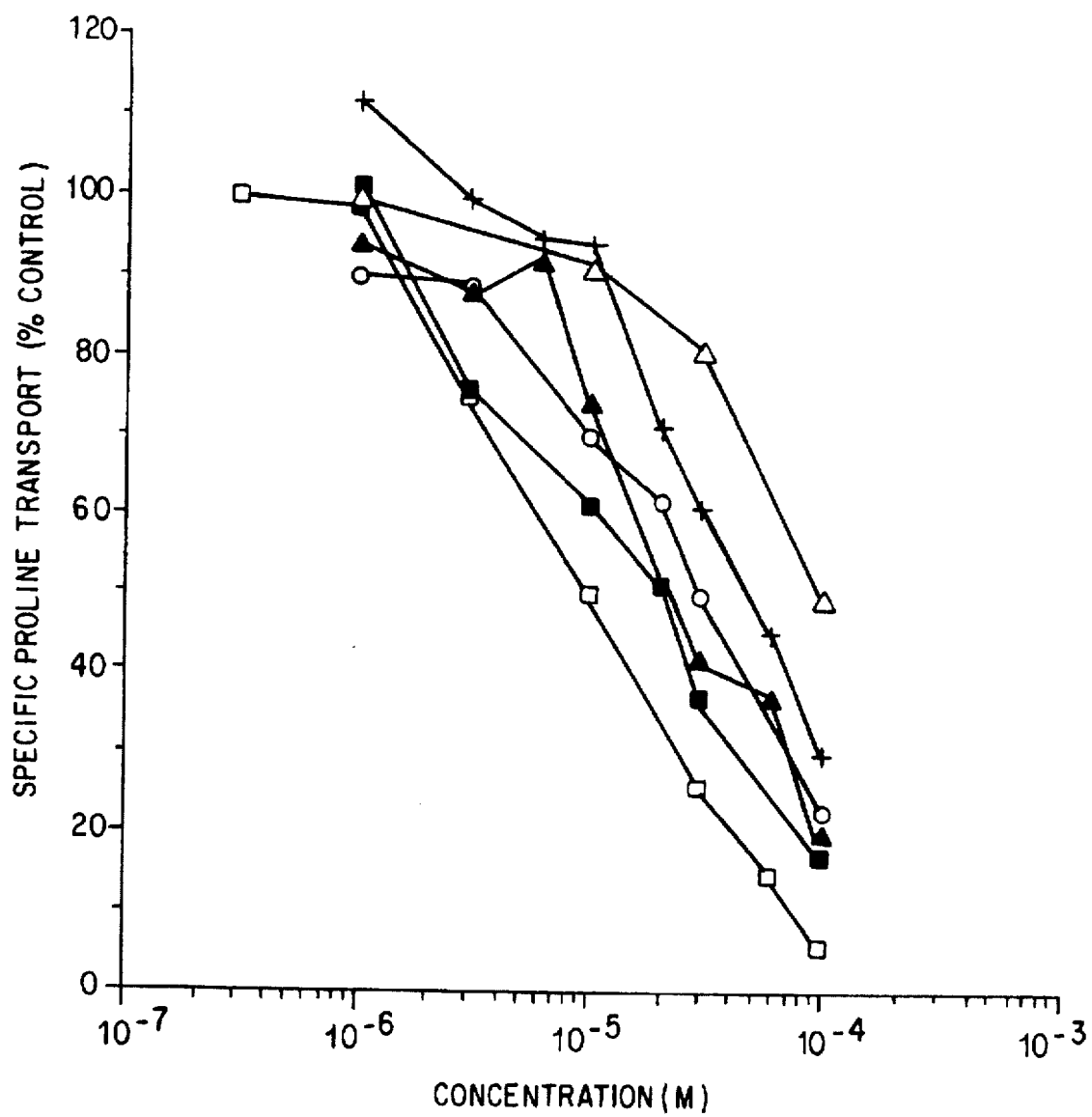
FIG. 4 is a graph of the inhibition of proline transport by structural analogs in transfected HeLa cells. Proline transport assays (50 nM L-([$^3$H]proline) were conducted for 20 minutes with or without increasing concentrations of the indicated pharmacological agents. The pharmacological agents are represented by the following symbols: open square symbol, L-proline; ■, L-pipecolic acid; ▲, sarcosine; open circle symbol, 3,4-dehydroproline; +, L-norleucine; and, open triangle symbol, L-azetidine-2-carboxylic acid. Nonspecific transport, determined by a parallel transfection of pBluescript SKII(–), was determined for each assay, and values were subtracted from signals obtained with rPROT. Data represent triplicate determinations of the percentage of specific proline uptake obtained with labeled substrate alone.

L-PROT-induced L-proline transport exhibited a marked stereospecificity. As described above, L-proline inhibited L[$^3$H]proline transport with low micromolar potency ($K_m$ approximately 9.7 µM). In contrast, D-proline only weakly inhibited transport ($K_i$ greater than 100M). A variety of proline analogs, excitatory amino acid analogs, and amino acids were tested for their ability to inhibit L-proline uptake in HeLa cells transiently transfected with pPROT (FIG. 4; Table 1; Table 2).

TABLE 1

Inhibitor Sensitivity of Proline Uptake in HeLa Cells Transfected with Rat Brain L-Proline Transporter cDNA.

| Inhibitor | $K_i$ (µM) |
|---|---|
| L-Pipecolic acid | 14 |
| Sarcosine | 30 |
| 3,4-Dehydroproline | 31 |
| L-Norleucine | 37 |
| L-Phenylalanine | 48 |
| L-Histidine | 83 |
| L-Cysteine | 91 |
| Azetidine-2-carboxylic acid | 115 |

HeLa cells (100–250,000 per well) infected with T7 RNA polymerase-containing vaccinia virus were transfected with pPROT (1 g) and incubated with 50 nM L-[$^3$H]proline with or without inhibitors for 20 min. at 37° C. $K_i$ values reflect mean estimates of triplicate determinations of uptake inhibition curves, adjusting for substrate concentration after Cheng and Prusoff (1973).

TABLE 2

Compounds with $K_i$ Values in Excess of 100 µM

Proline Analogs

L-Azetidine-2-carboxylic acid
N-acetylproline
1-Amino-1-cyclopropane carboxylic acid
3-Amino-1-hydroxy-2-pyrrolidone
Glycylproline
Hydroxyproline
D-Norleucine
(+/–)cis-2,3-piperidine dicarboxylic acid
L-Prolinamide
L-Proline methyl ester
Prolylglycine
Pyrrole-2-carboxylic acid Excitatory Amino Acid Analogs HA-966
Ibotenic acid
Kainic acid
N-methyl-D-aspartate
Quisqualic acid
Trans-ACPD
L-Trans-2,4-PDC Amino Acids L-Alanine
L-Arginine
L-Asparagine
D-Aspartic acid
L-Aspartic acid
L-Cystine
GABA
L-Glutamic acid
L-Glutamine
Glycine

TABLE 2-continued

Compounds with $K_i$ Values in Excess of 100 μM

L-Isoleucine
L-Leucine
L-Lysine
L-Methionine
D-Proline
L-Pyroglutamic acid
L-Serine
L-Threonine
L-Tryptophan
L-Tyrosine
L-Valine HeLa cells (100-250,000 per well) infected with a T7 RNA polymerase-containing vaccinia virus were transfected with pPROT (1 μg) and incubated with 50 nM L[$^3$H]proline with or without 100 μM inhibitors for 20 min at 37° C. in triplicate Abbreviations: HA-966, 3-amino-1-hydroxy-2-pyrrolidone; L-Trans-2,4-PDC, trans-L-pyrrolidone-2, 4-dicarboxylate; Trans-ACPD, trans-1-aminocyclopentane-1,3-dicarboxylic acid.

pPROT-induced L-proline transport was sensitive to pharmacological inhibition by the structurally related compounds L-pipecolic acid; sarcosine, 3,4-dehydroproline, and L-norleucine (FIG. 4), with the relative rank order of inhibition constants, $K_i$, of 14 μM, 31 μM, and 37 μM, respectively (Table 1). Of the amino acids examined, L-phenylalanine ($K_i$=48 μM), L-histidine ($K_i$=83 μM), and L-cysteine ($K_i$=91 μM) weakly inhibited L-proline uptake in transfected HeLa cells. Most L-amino acids and analogs, however, failed to inhibit high affinity L-proline transport with $K_i$ values in excess of 100 μM (Table 2). In particular, none of the excitatory amino acid analogs examined, including the specific L-glutamate uptake blocker, trans-L-pyrrolidone-2,4-dicarboxylate (L-trans-2,4-PDC) (Bridges et al., 1991), significantly inhibited L-proline uptake.

Previous kinetic studies of L-proline uptake in rat brain synaptosomes revealed two components of transport, one with high affinity ($K_m$=6–12 μM) and one with low affinity ($K_m$=190 μM) (Hauptman et al., 1983, FEBS Lett. 161, 301–305; Nadler, 1987, J.Neurochem. 49, 1155–1160). High affinity L-proline transport is unique to nervous tissue. In contrast, low affinity, Na$^+$-dependent L-proline transport has also been described in renal (Mircheff et al., 1982, J. Membr.Biol. 64, 113–122.; Hammerman and Sacktor, 1977, J. Biol. Chem. 252, 591–595) intestinal, (Stevens et al., 1984, Annu. Rev. Physiol. 46,417–433; Wright and Peerce, 1984, J. Biol. Chem. 259, 14993–14996), and choroid plexus (Ross and Wright, 1984, Res. 295, 155–160.) brush border membrane vesicles, rat brain capillaries (Hwang et al., 1983, J. Neurochem. 40, 317–323), and rat brain membrane vesicles (Kanner and Sharon, 1980, Biochim. Biophys. Acta 600, 185–194). The kinetic properties of the cloned transporter transiently expressed in HeLa cells indicate that this protein represents the high affinity L-proline transporter uniquely expressed in nervous tissue.

Several lines of evidence support a neurotransmitter or neuromodulatory role for L-proline in mammalian nervous tissue. First, regional differences in the CNS distribution of proline have been described. Second, a synaptosomal biosynthetic pathway of L-proline from ornithine has been described. Third, high affinity synaptosomal L-proline uptake exhibits a heterogeneous distribution in rodent CNS. The highest L-proline transport activities were observed in synaptosomes prepared from midbrain, caudate-putamen, hippocampus, and hypothalamus; lower activities were observed in the cerebral cortex and brain stem; and the lowest activities were observed in the cerebellum. Furthermore, high affinity, Na$^+$-dependent uptake of L-proline appears to be expressed by a subset of hippocampal glutamate pathways. Lesion studies indicated that the lateral perforant path, associational-commissural fibers in the dentate gyrus, and Schaffer collateral-commissural-ipsilateral stratum oriens fibers exhibit considerable L-proline uptake capacity; in contrast, the medial perforant path and the mossy fibers accumulate little or no L-proline. Fourth, exogenously loaded, radiolabeled L-proline is released from neocortical slices and synaptosomes in a Ca$^{2+}$-dependent manner in response to K$^+$-induced depolarization. Fifth, L-proline produces complex electrophysiological actions when iontophoresed onto neurons, producing excitatory or inhibitory actions on different types of neurons.

Many of the actions of L-proline in nervous tissue have been attributed to an interaction with excitatory glutamatergic neurotransmission. In situ hybridization results provide compelling support for a specific role for L-proline in certain excitatory pathways in the CNS. High levels of rPROT mRNA have been observed in putative glutamatergic cell bodies, including the mitral cells of the olfactory bulb, pyramidal cells of layer V of the cerebral cortex, pyramidal cells of the piriform cortex, the entorhinal cortex, and CA3 pyramidal cells of the hippocampus. In contrast, only low levels of rPROT mRNA were observed in the caudate-putamen, a brain region rich in glutamatergic nerve terminals presumably arising from glutamatergic pyramidal cells of layer V of the cerebral cortex. Based on the observation that the caudate-putamen exhibits high levels of synaptosomal L-proline transport but only low levels of rPROT mRNA, it appears that L-proline transporters are synthesized in putative glutamatergic pyramidal cells in layer V of the cerebral cortex and transported to axon terminals of these descending pathways in the caudate-putamen. The observation that rPROT mRNA is enriched in CA3 pyramidal cells of the hippocampus (see FIG. 1B) reinforces the conclusion that Na$^+$-dependent L-proline uptake is enriched in the terminal fields of the Schaffer collateral, commissural, and ipsilateral-associational projections of CA3 pyramidal cells. These neurons are believed to use an excitatory amino acid as a transmitter, and Na$^+$-dependent acidic amino acid transporters have been localized to nerve terminals of this pathway. The inability of L-glutamate, L-aspartate, and a range of structural analogs of glutamate and aspartate to inhibit L-proline transport induced by pPROT (Table 2) is consistent with the transport of L-proline and the acidic amino acids by distinct Na$^+$-dependent plasma membrane transporters that may coexist on the same synaptic terminals in subpopulations of glutamatergic neurons. The CA3-derived Schaffer collateral-commissural pathway has been implicated in associational memory processes exhibiting a robust form of long-term potentiation that is dependent upon the activation of N-methyl-D-aspartate receptors. This pathway may be the site where intracerebral injection of L-proline disrupts memory processes.

Although the presence of a high affinity, Na$^+$-dependent L-proline transporter in specific subpopulations of glutamatergic neurons is consistent with previous studies suggesting a specific postsynaptic role of L-proline at glutamate receptors, alternatives cannot be ruled out. For example, high affinity, Na$^+$-dependent l-proline uptake could alter presynaptic handling of the excitatory transmitter glutamate. Furthermore, L-proline could serve as a precursor for glutamate, however, the enzymes that are involved in this synthesis, proline oxidase and delta-pyrroline-5-carboxylate dehydrogenase, have been found in glial cells, not neurons.

The structural features of the high affinity rat brain L-proline transporter are virtually identical to those of the other cloned Na⁺-dependent neurotransmitter transporters, including the rat GABA, human NE, rat DA, and rat 5HT transporters. A tentative structural model for these proteins predicts the presence of approximately 12 transmembrane domains, cytoplasmic N- and C-termini, and a large, presumably glycosylated, extracellular loop separating transmembrane domains 3 and 4. Furthermore, despite dramatic differences in pharmacological sensitivities to substrates and antagonists, these transporters exhibit significant but dispersed amino acid sequence identities within or adjacent to the putative transmembrane domains. In particular, transmembrane domains 1, 2, 5, and 6 are the most well-conserved domains across the cloned transporters, exhibiting >43% amino acid sequence identity. These highly conserved transmembrane domains are likely to confer common functions to Na⁺-dependent neurotransmitter transporters, such as the maintenance of transporter topology, ion binding, and substrate translocation. In contrast, the least well-conserved domains across the cloned transporters are the cytoplasmic N- and C-terminal tails. Furthermore, transmembrane domains 3, 4, and 9–12 are poorly conserved, exhibiting less than 20% amino acid sequence identity. These poorly conserved domains may confer substrate-specific properties to the transporters.

Although a single cDNA can induce high affinity, Na⁺-dependent L-proline transport in transfected HeLa cells, the subunit stoichiometry of the native transporter complex has not been determined. The presence of a conserved leucine zipper motif in the second putative transmembrane domain of rPROT may mediate dimerization of proline transporter subunits in the membrane, as has been previously proposed for glucose transporters, or allow for heterotypic interactions with other membrane proteins with this motif. The ability of distinct K⁺ channel proteins to form heteromultimeric channels with properties that are different from those of homomultimeric channels warrants the consideration of heteromultimeric neurotransmitter transporters. Recent studies suggest that second messengers may regulate the activity of Na⁺-dependent neurotransmitter transporters. Within the putative intracellular domains of the high affinity rat brain L-proline transporter, several consensus sequences for protein kinase-mediated phosphorylation exist, and thus phosphorylation may regulate high affinity L-proline transport.

Protein can be expressed from the cDNA using standard techniques for expression in vitro in cell free translation systems, in bacteria, yeast, and animal cells, including insect, amphibian, avian, and mammalian cells, as well as genetically engineered, or transgenic, animals. The techniques are known to those skilled in the art. Reagents, including expression vectors and cell lines, for use in these methods, are commercially available from sources such as Promega and Stratagene.

It is understood that specific cDNA sequences can be modified by those skilled in the art, for example, by labelling, fusion with regulatory sequences, insertion into expression vectors, site-directed mutagenesis and substitution or deletion of nucleotides encoding specific amino acids, without departing from the scope of the nucleotide and amino acid sequences of the present invention, and the methods for their use.

The theories and standard procedures for molecular cloning are described in *Molecular Cloning*, edited by T. Maniatis, et al. Cold Spring Harbor, Laboratory, Cold Spring Harbor, N.Y.) and are generally known to those skilled in the art. Procedures include preparation of DNA and RNA, preparation of cloning vectors, ligation, transformation of competent cells, selection and screening by in situ filter hybridization, as described by David, et al., *Advanced Bacterial Genetics* (Cold Spring Harbor Laboratory, Cold Spring, N.Y.). In addition, techniques for separation of DNA by gel electrophoresis, mapping of restriction enzyme cleavage sites, and modification of DNA fragments by modifying enzymes are used. Most restriction enzymes, vectors, and reagents can be obtained from commercial companies. Common vectors and *E. coli* strains are used, for example, pBR322, pUC series, lambda-WES, M13mp, DH5, LE392, JM109 and HB101.

Chain termination methods are used for nucleotide sequence determination to confirm the DNA constructs at the splicing sites, as reported by Sanger, et al. *Proc. Natl. Acad. Sci. USA* 74, 5463 (1977). Many commercial suppliers provide both reagent kits and detailed protocols. Since most nucleotide sequences are known for the vectors, promoters and genes to be used, oligonucleotides of defined sequences are used as primers in sequencing experiments. These are typically 15 to 20 nucleotides long and very convenient for sequencing specific regions of interest, using the techniques of Messing, et al. *Nucleic Acids Res.* 9, 309 (1981). Either single-stranded or double-stranded DNA can be sequenced with this technique.

Oliogonucleotides to be used in DNA sequencing and polymerase chain reaction are synthesized by an automated DNA synthesizer. This service can be obtained from commercial sources, such as Genetic Designs, Inc., Houston, Tex. The oligonucleotides greater than 30 nucleotides are then subjected to polyacrylamide gel electrophoresis to ensure purity.

DNAs are transfected into cells by one of several standard published procedures to form stable transformants, including, for example, calcium phosphate precipitation, DEAE-Dextran, electroporation, and protoplast fusion. These methods are described in detail as follows:

Calcium phosphate precipitation: DNAs are coprecipitated with calcium phosphate, according to the method of Graham and VanDer in *Virology* 52, 456 (1973), before transfer into cells. 40–50 μg of DNA with salmon sperm or calf thymus DNA as carrier is used for $0.5 \times 10^6$ cells plated on a 100 mm dish. DNA is mixed with 0.5 ml of 2×Hepes solution (280 mM NaCl, 50 mM Hepes and 1.5 mM Na₂HPO₄, pH 7.0) to which an equal volume of 2×CaCl₂ (250 mM CaCl₂ and 10 mM Hepes, pH 7.0) is added. A white granular precipitate appearing after 30–40 minutes is distributed dropwise evenly on the cells and allowed to sit for 4–16 hours at 37° C. The medium is removed and the cells are shocked with 15% glycerol in PBS for 3 minutes. After removing the glycerol, the cells are fed with DMEM containing 10% fetal bovine serum and left in the incubator.

Protein samples are prepared for Western blot analysis by lysing cells and separating the proteins by SDS-PAGE. The proteins are transferred to nitrocellulose by electroblotting as described by Ausubek, et al., *Current Protocols in Molecular Biology* (John Wiley and Sons, 1987). After blocking the filter with instant nonfat dry milk (1 g in 100 ml PBS), primary antibody is added to the filter and incubated for 1 h at room temperature. The filter is washed thoroughly with phosphate buffered saline (PBS) and incubated with horseradish peroxidase (HRPO)-antibody conjugate for 1 hour at room temperature. The filter is again washed thoroughly with PBS and the antigen bands are identified by adding diaminobenzidine (DAB).

Enzyme assays, protein purification, and other classical biochemical methods are employed. DNA and RNA are analyzed by Southern blotting and Northern blotting techniques. Typically, the samples to be analyzed are size fractionated by gel electrophoresis. The samples, DNA or RNA, in the gels are then transferred to nitrocellulose or nylon membranes by blotting techniques. The blots, which are replicas of sample patterns in the gels, are hybridized with probes in Southern and Northern analysis. Specific bands of interest can then be visualized by detection systems such as autoradiography.

DNA can also be transferred using the DEAE-Dextran method of Kimura, et al. *Virology* 49, 394 (1972) and Sompayrac, et al., *Proc. Natl. Acad. Sci. USA* 78, 7575 (1981); the electroporation method of Potter, *Proc. Natl. Acad. Sci. USA* 81, 7161 (1984), and the protoplast fusion method of Sandri-Goddin, et al. *Molec. Cell Biol.* 1, 743 (1981).

Construction of Transgenic Animals:

The sequence provided herein can used to create transgenic animals in accordance with the method described in U.S. Pat. No. 4,873,191 to Wagner et al. Transgenic animals can also be prepared by the following method:

Animal Sources

Animals suitable for transgenic experiments can be obtained from standard commercial sources such as Charles River (Wilmington, Mass.), Taconic (Germantown, N.Y.), Harlan Sprague Dawley (Indianapolis, Ind.), etc. Swiss Webster female mice are preferred for embryo retrieval and transfer. B6D2F$_1$ males can be used for mating and vasectomized Swiss Webster studs can be used to stimulate pseudopregnancy. Vasectomized mice and rats can be obtained from the supplier.

Microinjection Procedures

The procedures for manipulation of the rodent embryo and for microinjection of DNA are described in detail in Hogan et al. Manipulating the mouse embryo, Cold Spring Harbor Labory, Cold Spring harbor, N.Y. (1986), the teachings of which are incorporated herein.

Transgenic Mice:

Female mice six weeks of age are induced to superovulate with a 5 IU injection (0.1 cc, ip) of pregnant mare serum gonadotropin (PMSG; Sigma) followed 48 hours later by a 5 IU injection (0.1 cc, ip) of human chorionic gonadotropin (hCG; Sigma). Females are placed with males immediately after hCG injection. Twenty-one hours after hCG, the mated females are sacrificed by $CO_2$ asphyxiation or cervical dislocation and embryos are recovered from excised oviducts and placed in Dulbecco's phosphate buffered saline with 0.5% bovine serum albumin (BSA; Sigma). Surrounding cumulus cells are removed with hyaluronidase (1 mg/ml). Pronuclear embryos are then washed and placed in Earle's balanced salt solution containing 0.5% BSA (EBSS) in a 37.5° C. incubator with a humidified atmosphere at 5% $CO_2$, 95% air until the time of injection.

Randomly cycling adult female mice are paired with vasectomized males. Swiss Webster or other comparable strains can be used for this purpose. Recipient females are mated at the same time as donor females. At the time of embryo transfer, the recipient females are anesthetized with an intraperitoneal injection of 0.015 ml of 2.5% avertin per gram of body weight. The oviducts are exposed by a single midline dorsal incision. An incision is then made through the body wall directly over the oviduct. The ovarian bursa is then torn with watchmakers forceps. Embryos to be transferred are placed in DPBS and in the tip of a transfer pipet (about 10–12 embryos). The pipet tip is inserted into the infundibulum and the embryos transferred. After the transfer, the incision is closed by two sutures.

Transgenic Rats:

The procedure for generating transgenic rats is similar to that of mice (Hammer et al., *Cell* 63;1099–112 (1990)).

Thirty day-old female rats are given a subcutaneous injection of 20 IU of PMSG (0.1 cc) and 48 hours later each female placed with a proven male. At the same time, 40–80 day old females are placed in cages with vasectomized males. These will provide the foster mothers for embryo transfer. The next morning females are checked for vaginal plugs. Females who have mated with vasectomized males are held aside until the time of transfer. Donor females that have mated are sacrificed ($CO_2$ asphyxiation) and their oviducts removed, placed in DPBS (Dulbecco's phosphate buffered saline) with 0.5% BSA and the embryos collected. Cumulus cells surronding the embryos are removed with hyaluronidase (1 mg/ml). The embryos are then washed and placed in EBSS (Earle's balanced salt solution) containing 0.5% BSA in a 37.5° C. incubator until the time of microinjection.

Once the embryos are injected, the live embryos are moved to DPBS for transfer into foster mothers. The foster mothers are anesthetized with ketamine (40 mg/kg, ip) and xylazine (5 mg/kg, ip). A dorsal midline incision is made through the skin and the ovary and oviduct are exposed by an incision through the muscle layer directly over the ovary. The ovarian bursa is torn, the embryos are picked up into the transfer pipet, and the tip of the transfer pipet is inserted into the infundibulum. Approximately 10–12 embryos are transferred into each rat oviduct through the infundibulum. The incision is then closed with sutures, and the foster mothers are housed singly.

Embryonic Stem (ES) Cell Methods

Introduction of cDNA into ES cells:

Methods for the culturing of ES cells and the subsequent production of transgenic animals, the introduction of DNA into ES cells by a variety of methods such as electroporation, calcium phosphate/DNA precipitation, and direct injection are described in detail in *Teratocarcinomas and embryonic stem cells, a practical approach*, ed. E. J. Robertson, (IRL Press 1987), the teachings of which are incorporated herein. Selection of the desired clone of transgene-containing ES cells is accomplished through one of several means. In cases involving random gene integration, an APP clone is co-precipitated with a gene encoding neomycin resistance. Transfection is carried out by one of several methods described in detail in Lovell-Badge, in *Teratocarcinomas and embryonic stem cells, a practical approach*, ed. E. J. Robertson, (IRL Press 1987) or in Potter et al *Proc. Natl. Acad. Sci. USA* 81, 7161 (1984). Calcium phosphate/DNA precipitation, direct injection, and electroporation are the preferred methods. In these procedures, $0.5 \times 10^6$ ES cells are plated into tissue culture dishes and transfected with a mixture of the linearized APP clone and 1 mg of pSV2neo DNA (Southern and Berg, *J. Mol Appl Gen.* 1:327–341 (1982)) precipitated in the presence of 50 mg lipofectin in a final volume of 100 µl. The cells are fed with selection medium containing 10% fetal bovine serum in DMEM supplemented with G418 (between 200 and 500 µg/ml). Colonies of cells resistant to G418 are isolated using cloning rings and expanded. DNA is extracted from drug resistant clones and Southern blotting experiments using an APP770 cDNA probe are used to identify those clones carrying the APP sequences. In some experiments, PCR methods are used to identify the clones of interest.

DNA molecules introduced into ES cells can also be integrated into the chromosome through the process of homologous recombination, described by Capecchi, (1989). Direct injection results in a high efficiency of integration. Desired clones are identified through PCR of DNA prepared from pools of injected ES cells. Positive cells within the pools are identified by PCR subsequent to cell cloning (Zimmer and Gruss, *Nature* 338, 150–153 (1989). DNA introduction by electroporation is less efficient and requires a selection step. Methods for positive selection of the recombination event (i.e., neo resistance) and dual positive-negative selection (i.e., neo resistance and gancyclovir resistance) and the subsequent identification of the desired clones by PCR have been described by Joyner et al., *Nature* 338, 153–156 (1989) and Capecchi, (1989), the teachings of which are incorporated herein.

Embryo Recovery and ES cell Injection:

Naturally cycling or superovulated female mice mated with males are used to harvest embryos for the implantation of ES cells. It is desirable to use the C57B strain for this purpose when using mice. Embryos of the appropriate age are recovered approximately 3.5 days after successful mating. Mated females are sacrificed by $CO_2$ asphyxiation or cervical dislocation and embryos are flushed from excised uterine horns and placed in Dulbecco's modified essential medium plus 10% calf serum for injection with ES cells. Approximately 10–20 ES cells are injected into blastocysts using a glass microneedle with an internal diameter of approximately 20 µm.

Transfer of Embryos to Pseudopregnant Females:

Randomly cycling adult female mice are paired with vasectomized males. Mouse strains such as Swiss Webster, ICR or others can be used for this purpose. Recipient females are mated such that they will be at 2.5 to 3.5 days post-mating when required for implantation with blastocysts containing ES cells. At the time of embryo transfer, the recipient females are anesthetized with an intraperitoneal injection of 0.015 ml of 2.5% avertin per gram of body weight. The ovaries are exposed by making an incision in the body wall directly over the oviduct and the ovary and uterus are externalized. A hole is made in the uterine horn with a 25 guage needle through which the blastocysts are transferred. After the transfer, the ovary and uterus are pushed back into the body and the incision is closed by two sutures. This procedure is repeated on the opposite side if additional transfers are to be made.

Identification of Transgenic Mice and Rats:

Tail samples (1–2 cm) are removed from three week old animals. DNA is prepared and analyzed by both Southern blot and PCR to detect transgenic founder ($F_0$) animals and their progeny ($F_1$ and $F_2$).

Transgenic animal prepared by these methods can be used for in vivo tests. This transgenic model allows simple and easy screening for pharmacologic agents capable of enhancing or decreasing levels of L-proline in brain synapses in vivo.

The sequence provided herein can also be used as a hybridization probe when labelled with a fluorescent or radiolabelled nucleotide. Probes can also be labelled using dyes, or enzymatic or chemiluminescent labels that are commercially available. These probes can be used to detect the expression of the high affinity L-proline transporter or related sequences in cells, tissue samples, or in in vitro reagents, as well as to screen samples from humans suspected of having an L-proline transporter disease or disorder. Levels of gene expression can be quantitated in patients and compared to healthy controls, or can be compared between different tissues.

The sequence provided herein encoding the high affinity L-proline transporter can be specifically used to isolate the sequence from other species, especially human.

The sequence provided herein can also be used to screen for compounds that modulate the expression or transport of proline by the transporter. The sequence can also be used to screen for compounds that bind directly to the high affinity L-proline transporter permitting its localization in situ and to screen for compounds that directly or indirectly interfere with L-proline transport. Compounds can be developed by conventional computer modelling methods as described below.

Computer Modeling.

Computer modeling technology allows visualization of the three-dimensional atomic structure of a selected molecule and the rational design of new compounds that will interact with the transporter molecule. The three-dimensional construct typically depends on data from x-ray crystallographic analyses or NMR imaging of the selected molecule. The molecular dynamics require force field data. The computer graphics systems enable prediction of how a new compound will link to the target molecule and allow experimental manipulation of the structures of the compound and target molecule to perfect binding specificity. Prediction of what the molecule-compound interaction will be when small changes are made in one or both requires molecular mechanics software and computationally intensive computers, usually coupled with user-friendly, menu-driven interfaces between the molecular design program and the user.

An example of the molecular modelling system described generally above consists of the CHARMm and QUANTA programs, Polygen Corporation, Waltham, Mass. CHARMm performs the energy minimization and molecular dynamics functions. QUANTA performs the construction, graphic modelling and analysis of molecular structure. QUANTA allows interactive construction, modification, visualization, and analysis of the behavior of molecules with each other.

A number of articles review computer modeling of drugs interactive with specific proteins, such as Rotivinen, et al., *Acta Pharmaceutica Fennica* 97, 159–166 (1988); Ripka, *New Scientist* 54–57 (Jun. 16, 1988); McKinaly and Rossmann, *Annu. Rev. Pharmacol. Toxiciol.* 29, 111–122 (1989); Perry and Davies, *OSAR: Quantitative Structure-Activity Relationships in Drug Design* pp. 189–193 (Alan R. Liss, Inc. 1989); Lewis and Dean, *Proc. R. Soc. Lond.* 236, 125–140 and 141–162 (1989); and, with respect to a model receptor for nucleic acid components, Askew, et al., *J. Am. Chem. Soc.* 111, 1082–1090 (1989).

Computer modelling has found limited use in the design of compounds that will interact with nucleic acids, because the generation of force field data and x-ray crystallographic information has lagged behind computer technology. CHARMm has been used for visualization of the three-dimensional structure of parts of four RNAs, as reported by Mei, et al., *Proc. Natl. Acad. Sci.* 86:9727 (1989), but computer modelling has not been used to design compounds that will bind to and inactivate RNA.

Other computer programs that screen and graphically depict chemicals are available from companies such as BioDesign, Inc., Pasadena, Calif., Allelix, Inc, Mississauga, Ontario, Canada, and Hypercube, Inc., Cambridge, Ontario. Although these are primarily designed for application to drugs specific to particular proteins, they can be adapted to design of drugs specific to regions of RNA, once that region is identified.

Synthesis of Transporter Modulating Compounds.

Compounds which specifically inhibit the function of the transporter molecule are synthesized using methods known to those skilled in the art based on the sequence and structure determined as described above. Known compounds can also be modified or selected on the basis of their existing structure, once the requirements for specificity are known.

The compounds can be organic, inorganic, proteins, or even other nucleic acids. Specific binding to the targeted molecule can be achieved by including in the molecule complementary nucleic acid sequence that forms base pairs with the transporter sequence under appropriate conditions, or by inclusion of chemical groups having the correct spatial location and charge.

In the preferred embodiments, compounds are designed as a peptide or organic compound with hydrogen bond donor and acceptor sites arranged to be complementary to the cDNA.

For peptides, the proposed hydrogen acceptors are the carbonyl oxygens of the peptide backbone; the side chains of glutamic acid, aspartic acid, asparagine, glutamine; and the imidazole nitrogen of histidine. The proposed hydrogen bond donors are the backbone amides N—H; the side chain hydroxyl groups of serine, threonine, and tyrosine; the sulfhydryl of cysteine; the indole of N—H of tryptophan; the guanidino group of arginine; the $NH_2$ of glutamine and asparagine; and the N—H of imidazole side chain of histidine.

A peptide is formed with the amino acids ordered to yield the correct spatial arrangement of hydrogen bond acceptors and donors, when the peptide is in a specific conformation induced and stabilized by binding to the target cDNA segment. The likelihood of forming the desired conformation can be refined and/or optimized using molecular computational programs.

Organic compounds can be designed to be rigid, or to present hydrogen bonding groups on edge or plane, which can interact with complementary sites. Rebek, *Science* 235, 1478–1484 (1987) and Rebek, et al., *J. Am. Chem. Soc.* 109, 2426–2431 (1987), have summarized some of these approaches and the mechanisms involved in binding of compounds to regions of proteins.

In some cases, the inhibitory compound is a nucleic acid molecule, either RNA or DNA. This can be prepared synthetically using commercially available equipment or by cloning of an appropriate sequence which is designed or derived from the sequence to be inhibited.

The methods, reagents, and computer software programs described in the references cited herein are specifically incorporated by reference. Other methods and materials useful for molecular modeling and chemical synthesis are known to those skilled in the art.

Antibodies

Expressed protein can also be used to immunize animals to generate polyclonal antisera and/or monoclonal antibodies useful in detection and localization of the transporter in accordance with methods well known to those skilled in the art.

Modifications and variations of the present invention, nucleic acid sequence encoding a high affinity, $Na^+$-dependent L-proline transporter, and the encoded protein, as well as methods of use thereof, will be obvious to those skilled in the art from the foregoing detailed description. Such modifications and variations are intended to come within the scope of the appended claims.

We claim:

1. An isolated and purified polypeptide comprising the amino acid sequence of a high affinity, Na⁺-dependent L-proline transporter expressed in mammalian brain, wherein said transporter is encoded by a nucleic acid molecule that hybridizes under standard conditions to a nucleic acid molecule complementary to the full length of SEQ ID NO: 7.

2. A polypeptide according to claim 1, comprising the amino acid sequence set forth in SEQ ID NO: 8.

3. A polypeptide according to claim 1, having the amino acid sequence set forth in SEQ ID NO: 8.

4. An isolated antibody specifically reactive with a high affinity, Na⁺-dependent L-proline transporter expressed in mammalian brain, wherein said transporter is encoded by a nucleic acid molecule that hybridizes under standard conditions to a nucleic acid molecule complementary to the full length of SEQ ID NO: 7, wherein said antibody does not cross-react with any other neurotransmitter transporter.

5. An antibody according to claim 4, wherein said antibody is polyclonal.

6. An antibody according to claim 4, wherein said antibody is monoclonal.

7. An antibody according to claim 4, wherein said antibody is specifically reactive with a polypeptide having the amino acid sequence set forth in SEQ ID NO: 8.

8. A method for detecting the presence of a mammalian L-proline transporter polypeptide in a sample, comprising the steps of:

contacting a sample containing one or more proteins with an antibody according to claim 4 under conditions suitable for the binding of the antibody to proteins with which it is specifically reactive;

separating unbound antibody from the one or more proteins; and detecting antibody which remains bound to one or more of the proteins in the sample.

9. A method for detecting the presence of a mammalian L-proline transporter polypeptide, comprising the steps of:

contacting a sample containing one or more proteins with an antibody according to claim 4 under conditions suitable for the binding of the antibody to proteins with which it is specifically reactive;

separating unbound proteins from the antibody; and detecting antibody which remains bound to one or more of the proteins in the sample.

10. A method according to claim 8 or 9, wherein said antibody is polyclonal.

11. A method according to claim 8 or 9, wherein said antibody is monoclonal.

12. A method according to claim 8 or 9, wherein said antibody is specifically reactive with a polypeptide having the amino acid sequence set forth in SEQ ID NO: 8.

13. A method according to claim 12, wherein said antibody is polyclonal.

14. A method according to claim 12, wherein said antibody is monoclonal.

* * * * *

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v i ) ORIGINAL SOURCE:
        ( A ) ORGANISM: Rattus ( i x ) FEATURE:
        ( A ) NAME/KEY: Domain
        ( B ) LOCATION: 1..7
        ( D ) OTHER INFORMATION: /note= "Synthetic degenerate oligonucleotide primer"

( x i ) SEQUENCE DESCRIPTION: SEQ ID NO:1:

```
Asn  Val  Trp  Arg  Phe  Pro  Tyr
1                  5
```

( 2 ) INFORMATION FOR SEQ ID NO:2:

( i ) SEQUENCE CHARACTERISTICS:
        ( A ) LENGTH: 7 amino acids
        ( B ) TYPE: amino acid (C) STRANDEDNESS: single
(D) TOPOLOGY: linear (ii) MOLECULE TYPE: peptide (iii) HYPOTHETICAL: NO (iv) ANTI-SENSE: NO (vi) ORIGINAL SOURCE:
    (A) ORGANISM: Rattus (ix) FEATURE:
    (A) NAME/KEY: Domain
    (B) LOCATION: 1..7
    (D) OTHER INFORMATION: /note= "Synthetic degenerate oligonucleotide primer"

(xi) SEQUENCE DESCRIPTION: SEQ ID NO:2:

Trp Ile Asp Ala Ala Thr Gln
1               5

(2) INFORMATION FOR SEQ ID NO:3:

(i) SEQUENCE CHARACTERISTICS:
    (A) LENGTH: 29 base pairs
    (B) TYPE: nucleic acid
    (C) STRANDEDNESS: single
    (D) TOPOLOGY: linear (ii) MOLECULE TYPE: cDNA (iii) HYPOTHETICAL: NO (iv) ANTI-SENSE: NO (vi) ORIGINAL SOURCE:
    (A) ORGANISM: Rattus (ix) FEATURE:
    (A) NAME/KEY: misc_feature
    (B) LOCATION: 1..29
    (D) OTHER INFORMATION: /note= "Synthetic, degenerate oligonucleotide"

(xi) SEQUENCE DESCRIPTION: SEQ ID NO:3:

CCGCTCGAGA AYGTSTGGCG STTYCCNTA    29

(2) INFORMATION FOR SEQ ID NO:4:

(i) SEQUENCE CHARACTERISTICS:
    (A) LENGTH: 30 base pairs
    (B) TYPE: nucleic acid
    (C) STRANDEDNESS: single
    (D) TOPOLOGY: linear (ii) MOLECULE TYPE: cDNA (iii) HYPOTHETICAL: NO (iv) ANTI-SENSE: NO (vi) ORIGINAL SOURCE:
    (A) ORGANISM: Rattus
    (F) TISSUE TYPE: Brain (ix) FEATURE:
    (A) NAME/KEY: misc_feature
    (B) LOCATION: 1..30
    (D) OTHER INFORMATION: /note= "Synthetic, degenerate oligonucleotide"

(ix) FEATURE:
    (A) NAME/KEY: misc_feature
    (B) LOCATION: 16..17
    (D) OTHER INFORMATION: /note= "N at position 16 identifies Inosine."

( x i ) SEQUENCE DESCRIPTION: SEQ ID NO:4:

GCTCTAGAGC TGRGTNGCRC CRTCRAKCCA 30

( 2 ) INFORMATION FOR SEQ ID NO:5:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Rattus ( v i i ) IMMEDIATE SOURCE:
        ( B ) CLONE: PCR fragment rTB2-2

( i x ) FEATURE:
        ( A ) NAME/KEY: misc_feature
        ( B ) LOCATION: 1..22
        ( D ) OTHER INFORMATION: /note= "Oligonucleotide"

( x i ) SEQUENCE DESCRIPTION: SEQ ID NO:5:

AACGGTGGCG CTTTCCTTAT CG 22

( 2 ) INFORMATION FOR SEQ ID NO:6:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( v i i ) IMMEDIATE SOURCE:
        ( B ) CLONE: PCR fragment rTB2-2

( i x ) FEATURE:
        ( A ) NAME/KEY: misc_feature
        ( B ) LOCATION: 1..21
        ( D ) OTHER INFORMATION: /note= "Oligonucleotide"

( x i ) SEQUENCE DESCRIPTION: SEQ ID NO:6:

TGCACCCGCA CCTTTGAAGA G 21

( 2 ) INFORMATION FOR SEQ ID NO:7:

( i ) SEQUENCE CHARACTERISTICS:
        ( A ) LENGTH: 2728 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Rattus (F) TISSUE TYPE: Brain (vii) IMMEDIATE SOURCE:
    (A) LIBRARY: rat forebrain cDNA library
    (B) CLONE: rTB2-2-20

(xi) SEQUENCE DESCRIPTION: SEQ ID NO:7:

| | | | | | | |
|---|---|---|---|---|---|---|
| TATCTCAAAG | GCGCAGAGAT | AGGACCAGTG | CTCGGCGCCC | GCTTGGCTGG | CTGACTGCGC | 60 |
| TCTTGCAAGC | ACCGGTGCCA | GCTCTCCAAG | ATGAAGAAGC | TCCAGGAAGC | TCACCTCCGC | 120 |
| AAGCCTGTCA | CCCCAGACCT | GCTGATGACT | CCCAGTGACC | AGGGTGATGT | GGACCTGGAT | 180 |
| GTAGACTTTG | CAGCAGACAG | AGGCAACTGG | ACGGGCAAGC | TGGACTTCTT | GCTGTCCTGC | 240 |
| ATCGGCTACT | GTGTGGGCTT | GGGAAATGTC | TGGCGGTTTC | CTATCGAGC | CTACACCAAT | 300 |
| GGAGGCGGAG | CCTTCCTCGT | GCCCTACTTC | CTCATGCTGG | CCATCTGTGG | CATCCCCTC | 360 |
| TTCTTTCTTG | AGCTCTCCCT | GGGCCAGTTC | TCCAGCCTGG | GACCCCTGGC | TGTCTGGAAA | 420 |
| ATCAGCCCCC | TCTTCAAAGG | TGCGGGTGCA | GCCATGCTGC | TCATCGTGGG | CCTGGTGGCC | 480 |
| ATCTACTACA | ACATGATCAT | CGCCTACGTC | CTCTTCTACC | TCTTCGCCTC | CCTCACCAGC | 540 |
| AACCTGCCCT | GGGAGCATTG | CGGCAACTGG | TGGAACACAG | AACGCTGCCT | GGAGCACAGA | 600 |
| GGCCCCAAGG | ATGGCAACGG | GGCACTGCCT | CTTAACCTCA | GCAGCACTGT | CAGCCCCAGT | 660 |
| GAGGAGTACT | GGAGCCGATA | TGTCCTGCAC | ATTCAGGGCA | GCCAGGGCAT | CGGCCGACCC | 720 |
| GGGGAGATTC | GCTGGAACCT | CTGCCTCTGC | CTGCTGCTGG | CCTGGGTCAT | CGTGTTTCTC | 780 |
| TGTATCCTGA | AGGGGGTGAA | GTCCTCGGGC | AAGGTGGTGT | ATTTCACAGC | CACCTTTCCC | 840 |
| TACCTCATCC | TGCTCATGCT | CCTGGTTCGA | GGAGTGACCC | TTCCCGGGGC | CTGGAAGGGC | 900 |
| ATCCAGTTCT | ATCTCACCCC | CCAATTCCAC | CACCTGCTGT | CTTCCAAGGT | GTGGATTGAA | 960 |
| GCTGCTCTTC | AGATCTTCTA | CTCTCTAGGA | GTGGGTTTTG | GGGTCTTCT | CACCTTTGCC | 1020 |
| TCCTACAACA | CATTCCACCA | GAACATCTAC | AGAGACACCT | TCATTGTCAC | CTGGGCAAT | 1080 |
| GCCATCACCA | GCATCCTGGC | TGGTTTTGCT | ATCTTCTCGG | TGCTGGGCTA | CATGTCGCAG | 1140 |
| GAGCTGGGTG | TGCCTGTGGA | CCAAGTGGCC | AAAGCAGGCC | CTGGCCTGGC | CTTTGTTATC | 1200 |
| TACCCACAGG | CCATGACTAT | GTTGCCTCTG | TCACCCTTCT | GGTCCTTCCT | CTTCTTCTTC | 1260 |
| ATGCTTCTGA | CTCTTGGCCT | CGATAGCCAG | TTTGCCTTTC | TGGAAACCAT | AGTGACTGCA | 1320 |
| GTGACCGATG | AGTTCCCATA | CTACCTACGG | CCCAAGAAGG | CAGTGTTCTC | AGGCCTCATC | 1380 |
| TGTGTAGCCA | TGTACCTGAT | GGGACTGATC | CTCACCACCG | ATGGGGGAT | GTACTGGCTG | 1440 |
| GTCCTTCTGG | ATGACTACAG | CGCCAGCTTC | GGACTCATGG | TGGTGGTGAT | TACCACATGC | 1500 |
| CTCGCTGTCA | CCCGGGTATA | CGGCATCCAG | CGGTTTTGTC | GTGACATCCA | CATGATGCTG | 1560 |
| GGCTTCAAGC | CAGGACTCTA | CTTCAGGGCC | TGCTGGCTGT | TTTTGTCTCC | GGCCACACTC | 1620 |
| TTGGCCTTGC | TGGTGTACAG | TATCGTCAAG | TACCAGCCCT | CGGAATACGG | TAGCTATCGC | 1680 |
| TTCCCCGCCT | GGGCCGAGCT | GCTAGGCATC | CTGATGGGCC | TGCTCTCCTG | CCTCATGATC | 1740 |
| CCAGCTGGCA | TGCTGGTAGC | TGTGCTTCGA | GAGGAGGGCT | CGCTCTGGGA | GCGACTTCAG | 1800 |
| CAAGCCAGCC | GTCCTGCTAT | AGACTGGGGC | CCATCACTGG | AAGAGAACCG | GACGGGCATG | 1860 |
| TATGTGGCCA | CCCTGGCTGG | GAGCCAGTCA | CCAAAACCAC | TGATGGTACA | CATGCGAAAA | 1920 |
| TATGGGGGCA | TCACCAGCTT | CGAGAATACA | GCCATTGAGG | TGGACCGTGA | GATCGCAGAG | 1980 |
| GAGGAAGAGG | AGTCCATGAT | GTGAGACCAG | ACACCTCCAA | ACAGGAGGGC | TGGTCGGGGC | 2040 |
| CTCCCCGTCT | GTCCCTTCCT | TGGCCACAGG | GGATAGCTTT | GTCTGTTGGG | ATTCTGACAG | 2100 |
| GCAATGGGAG | GTTGCCATGG | CAACGACAGT | CCCCAGCCTA | AGTCCCTCTT | TGTGGCCTCT | 2160 |

| | | | | | | |
|---|---|---|---|---|---|---|
| ACATCTCCTG | GAACCTCTAG | ATGGACATAC | ATATACTAGG | TAACCCATTC | AAAGCTGAAA | 2220 |
| CGATTCAGCT | CAGCCCTCAG | TTTGTGAGGG | GGTGCGTTGA | AGCCAGGGAG | AGAAGAGCTG | 2280 |
| GACCAAGGTG | ACATGCCCAA | GAGGACTTGT | TCCCAAGCCT | CCTCCAGCCA | GTCAACTCCC | 2340 |
| TTTCCCTTGG | GGGAGCAAGC | ACCATATCTG | ACATCTTTGT | TCAGACACTT | TGACAAGATA | 2400 |
| CATTTCCATA | CAAGCCAACT | TTAAACCCCA | GGTTCAGGGT | AGCGAGAACC | TGGAGAGCCC | 2460 |
| CAAGGCCCTG | GATATAGATA | GAATGGCAGC | GACCAAATTG | GGTAGAAAAG | TCTTTGTGGG | 2520 |
| TTCCTGTGTT | AAGGCCAGTT | TTCCCAGAAG | AAGTGGGAGC | TTTAGGGCTG | AGAGGTGTGA | 2580 |
| AAGATTGCAG | AAGAGGCTAG | AGGGAAGGTT | TGCGGGTCAG | AGCTGCCCCT | GAGCCAGGAG | 2640 |
| GAGGCCCAAC | CTGCCAGAGC | AGAGACCAGG | AGGGGCTGGA | GATTGTGGTG | CTCCCGGGTT | 2700 |
| ATGAGAGGGA | ATAAAGACTC | GCAGGGCC | | | | 2728 |

( 2 ) INFORMATION FOR SEQ ID NO:8:

( i ) SEQUENCE CHARACTERISTICS:
        ( A ) LENGTH: 667 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( v i ) ORIGINAL SOURCE:
        ( A ) ORGANISM: Rattus
        ( F ) TISSUE TYPE: Brain ( v i i ) IMMEDIATE SOURCE:
        ( A ) LIBRARY: rat forebrain cDNA library
        ( B ) CLONE: rTB2-2-20

( i x ) FEATURE:
        ( A ) NAME/KEY: Domain
        ( B ) LOCATION: 76..95
        ( D ) OTHER INFORMATION: /note= "Membrane-spanning domain"

( i x ) FEATURE:
        ( A ) NAME/KEY: Domain
        ( B ) LOCATION: 103..127
        ( D ) OTHER INFORMATION: /note= "Membrane-spanning domain"

( i x ) FEATURE:
        ( A ) NAME/KEY: Domain
        ( B ) LOCATION: 147..167
        ( D ) OTHER INFORMATION: /note= "Membrane-spanning domain"

( i x ) FEATURE:
        ( A ) NAME/KEY: Domain
        ( B ) LOCATION: 247..266
        ( D ) OTHER INFORMATION: /note= "Membrane-spanning domain"

( i x ) FEATURE:
        ( A ) NAME/KEY: Domain
        ( B ) LOCATION: 272..294
        ( D ) OTHER INFORMATION: /note= "Membrane-spanning domain"

( i x ) FEATURE:
        ( A ) NAME/KEY: Domain
        ( B ) LOCATION: 321..341
        ( D ) OTHER INFORMATION: /note= "Membrane-spanning domain"

( i x ) FEATURE:
        ( A ) NAME/KEY: Domain
        ( B ) LOCATION: 353..375
        ( D ) OTHER INFORMATION: /note= "Membrane-spanning domain"

( i x ) FEATURE:
    ( A ) NAME/KEY: Domain
    ( B ) LOCATION: 404..427
    ( D ) OTHER INFORMATION: /note= "Membrane-spanning domain"

( i x ) FEATURE:
    ( A ) NAME/KEY: Domain
    ( B ) LOCATION: 454..473
    ( D ) OTHER INFORMATION: /note= "Membrane-spanning domain"

( i x ) FEATURE:
    ( A ) NAME/KEY: Domain
    ( B ) LOCATION: 487..509
    ( D ) OTHER INFORMATION: /note= "Membrane-spanning domain"

( i x ) FEATURE:
    ( A ) NAME/KEY: Domain
    ( B ) LOCATION: 530..549
    ( D ) OTHER INFORMATION: /note= "Membrane-spanning domain"

( i x ) FEATURE:
    ( A ) NAME/KEY: Domain
    ( B ) LOCATION: 567..589
    ( D ) OTHER INFORMATION: /note= "Membrane-spanning domain"

( i x ) FEATURE:
    ( A ) NAME/KEY: Region
    ( B ) LOCATION: 44..45
    ( D ) OTHER INFORMATION: /note= "protein kinase C
          phosphorylation site"

( i x ) FEATURE:
    ( A ) NAME/KEY: Region
    ( B ) LOCATION: 71..72
    ( D ) OTHER INFORMATION: /note= "cAMP-dependent protein
          kinase phosphorylation site"

( i x ) FEATURE:
    ( A ) NAME/KEY: Region
    ( B ) LOCATION: 269..270
    ( D ) OTHER INFORMATION: /note= "protein kinase C
          phosphorylation site"

( i x ) FEATURE:
    ( A ) NAME/KEY: Region
    ( B ) LOCATION: 630..631
    ( D ) OTHER INFORMATION: /note= "protein kinase C
          phosphorylation site"

( i x ) FEATURE:
    ( A ) NAME/KEY: Region
    ( B ) LOCATION: 106..127
    ( D ) OTHER INFORMATION: /note= "Leucine zipper motif"

( i x ) FEATURE:
    ( A ) NAME/KEY: Region
    ( B ) LOCATION: 212..213
    ( D ) OTHER INFORMATION: /note= "N-linked glycosylation
          site"

( x i ) SEQUENCE DESCRIPTION: SEQ ID NO:8:

```
Pro Arg Leu Ile Asn Glu Thr Arg Ala Asn Ser Pro Arg Thr Glu Arg
1               5                   10                  15

Pro Glu Pro Thr Ile Asp Glu Ser Glu Gln Glu Asn Cys Glu Met Lys
            20                  25                  30

Lys Leu Gln Glu Ala His Leu Arg Lys Pro Val Thr Pro Asp Leu Leu
            35                  40                  45

Met Thr Pro Ser Asp Gln Gly Asp Val Asp Leu Asp Val Asp Phe Ala
        50                  55                  60

Ala Asp Arg Gly Asn Trp Thr Gly Lys Leu Asp Phe Leu Leu Ser Cys
65                  70                  75                  80

Ile Gly Tyr Cys Val Gly Leu Gly Asn Val Trp Arg Phe Pro Tyr Arg
                85                  90                  95
```

-continued

| | | | | | | | | | | | | | | |
|---|---|---|---|---|---|---|---|---|---|---|---|---|---|---|
| Ala | Tyr | Thr | Asn 100 | Gly | Gly | Gly | Ala | Phe 105 | Leu | Val | Pro | Tyr 110 | Leu | Met |
| Leu | Ala | Ile 115 | Cys | Gly | Ile | Pro | Leu 120 | Phe | Phe | Leu | Glu | Leu 125 | Ser | Leu | Gly |
| Gln | Phe 130 | Ser | Ser | Leu | Gly | Pro 135 | Leu | Ala | Val | Trp | Lys 140 | Ile | Ser | Pro | Leu |
| Phe 145 | Lys | Gly | Ala | Gly | Ala 150 | Ala | Met | Leu | Leu | Ile 155 | Val | Gly | Leu | Val | Ala 160 |
| Ile | Tyr | Tyr | Asn | Met 165 | Ile | Ile | Ala | Tyr | Val 170 | Leu | Phe | Tyr | Leu | Phe 175 | Ala |
| Ser | Leu | Thr | Ser 180 | Asn | Leu | Pro | Trp | Glu 185 | His | Cys | Gly | Asn | Trp 190 | Trp | Asn |
| Thr | Glu | Arg 195 | Cys | Leu | Glu | His | Arg 200 | Gly | Pro | Lys | Asp | Gly 205 | Asn | Gly | Ala |
| Leu | Pro 210 | Leu | Asn | Leu | Ser | Ser 215 | Thr | Val | Ser | Pro | Ser 220 | Glu | Glu | Tyr | Trp |
| Ser 225 | Arg | Tyr | Val | Leu | His 230 | Ile | Gln | Gly | Ser | Gln 235 | Gly | Ile | Gly | Arg | Pro 240 |
| Gly | Glu | Ile | Arg | Trp 245 | Asn | Leu | Cys | Leu | Cys 250 | Leu | Leu | Leu | Ala | Trp 255 | Val |
| Ile | Val | Phe | Leu 260 | Cys | Ile | Leu | Lys | Gly 265 | Val | Lys | Ser | Ser | Gly 270 | Lys | Val |
| Val | Tyr | Phe 275 | Thr | Ala | Thr | Phe | Pro 280 | Tyr | Leu | Ile | Leu | Leu 285 | Met | Leu | Leu |
| Val | Arg 290 | Gly | Val | Thr | Leu | Pro 295 | Gly | Ala | Trp | Lys | Gly 300 | Ile | Gln | Phe | Tyr |
| Leu 305 | Thr | Pro | Gln | Phe | His 310 | His | Leu | Leu | Ser | Ser 315 | Lys | Val | Trp | Ile | Glu 320 |
| Ala | Ala | Leu | Gln | Ile 325 | Phe | Tyr | Ser | Leu | Gly 330 | Val | Gly | Phe | Gly | Gly 335 | Leu |
| Leu | Thr | Phe | Ala 340 | Ser | Tyr | Asn | Thr | Phe 345 | His | Gln | Asn | Ile | Tyr 350 | Arg | Asp |
| Thr | Phe | Ile 355 | Val | Thr | Leu | Gly | Asn 360 | Ala | Ile | Thr | Ser | Ile 365 | Leu | Ala | Gly |
| Phe | Ala 370 | Ile | Phe | Ser | Val | Leu 375 | Gly | Tyr | Met | Ser | Gln 380 | Glu | Leu | Gly | Val |
| Pro 385 | Val | Asp | Gln | Val | Ala 390 | Lys | Ala | Gly | Pro | Gly 395 | Leu | Ala | Phe | Val | Ile 400 |
| Tyr | Pro | Gln | Ala | Met 405 | Thr | Met | Leu | Pro | Leu 410 | Ser | Pro | Phe | Trp | Ser 415 | Phe |
| Leu | Phe | Phe | Phe 420 | Met | Leu | Leu | Thr | Leu 425 | Gly | Leu | Asp | Ser | Gln 430 | Phe | Ala |
| Phe | Leu | Glu 435 | Thr | Ile | Val | Thr | Ala 440 | Val | Thr | Asp | Glu | Phe 445 | Pro | Tyr | Tyr |
| Leu | Arg 450 | Pro | Lys | Lys | Ala | Val 455 | Phe | Ser | Gly | Leu | Ile 460 | Cys | Val | Ala | Met |
| Tyr 465 | Leu | Met | Gly | Leu | Ile 470 | Leu | Thr | Thr | Asp | Gly 475 | Gly | Met | Tyr | Trp | Leu 480 |
| Val | Leu | Leu | Asp | Asp 485 | Tyr | Ser | Ala | Ser | Phe 490 | Gly | Leu | Met | Val | Val 495 | Val |
| Ile | Thr | Thr | Cys 500 | Leu | Ala | Val | Thr | Arg 505 | Val | Tyr | Gly | Ile | Gln 510 | Arg | Phe |
| Cys | Arg | Asp 515 | Ile | His | Met | Met | Leu 520 | Gly | Phe | Lys | Pro | Gly 525 | Leu | Tyr | Phe |

| | | | | | | | | | | | | | |
|---|---|---|---|---|---|---|---|---|---|---|---|---|---|
| Arg | Ala | Cys | Trp | Leu | Phe | Leu | Ser | Pro | Ala | Thr | Leu | Leu | Ala | Leu | Leu |
| | 530 | | | | 535 | | | | 540 | | | | |
| Val | Tyr | Ser | Ile | Val | Lys | Tyr | Gln | Pro | Ser | Glu | Tyr | Gly | Ser | Tyr | Arg |
| 545 | | | | 550 | | | | | 555 | | | | 560 |
| Phe | Pro | Ala | Trp | Ala | Glu | Leu | Leu | Gly | Ile | Leu | Met | Gly | Leu | Leu | Ser |
| | | | 565 | | | | | 570 | | | | | 575 |
| Cys | Leu | Met | Ile | Pro | Ala | Gly | Met | Leu | Val | Ala | Val | Leu | Arg | Glu | Glu |
| | | | 580 | | | | | 585 | | | | | 590 |
| Gly | Ser | Leu | Trp | Glu | Arg | Leu | Gln | Gln | Ala | Ser | Arg | Pro | Ala | Ile | Asp |
| | | 595 | | | | | 600 | | | | | 605 | | |
| Trp | Gly | Pro | Ser | Leu | Glu | Glu | Asn | Arg | Thr | Gly | Met | Tyr | Val | Ala | Thr |
| | 610 | | | | | 615 | | | | | 620 | | | | |
| Leu | Ala | Gly | Ser | Gln | Ser | Pro | Lys | Pro | Leu | Met | Val | His | Met | Arg | Lys |
| 625 | | | | | 630 | | | | | 635 | | | | | 640 |
| Tyr | Gly | Gly | Ile | Thr | Ser | Phe | Glu | Asn | Thr | Ala | Ile | Glu | Val | Asp | Arg |
| | | | | 645 | | | | | 650 | | | | | 655 | |
| Glu | Ile | Ala | Glu | Glu | Glu | Glu | Glu | Ser | Met | Met | | | | | |
| | | | 660 | | | | | 665 | | | | | | | |

( 2 ) INFORMATION FOR SEQ ID NO:9:

( i ) SEQUENCE CHARACTERISTICS:
        ( A ) LENGTH: 635 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( v i ) ORIGINAL SOURCE:
        ( A ) ORGANISM: Rattus
        ( F ) TISSUE TYPE: Brain - Proline Transporter ( i x ) FEATURE:
        ( A ) NAME/KEY: Domain
        ( B ) LOCATION: 46..65
        ( D ) OTHER INFORMATION: /note= "Proposed transmembrane
            domain."

( i x ) FEATURE:
        ( A ) NAME/KEY: Domain
        ( B ) LOCATION: 72..97
        ( D ) OTHER INFORMATION: /note= "Proposed transmembrane
            domain."

( i x ) FEATURE:
        ( A ) NAME/KEY: Domain
        ( B ) LOCATION: 117..137
        ( D ) OTHER INFORMATION: /note= "Proposed transmembrane
            domain."

( i x ) FEATURE:
        ( A ) NAME/KEY: Domain
        ( B ) LOCATION: 217..236
        ( D ) OTHER INFORMATION: /note= "Proposed transmembrane
            domain."

( i x ) FEATURE:
        ( A ) NAME/KEY: Domain
        ( B ) LOCATION: 243..264
        ( D ) OTHER INFORMATION: /note= "Proposed transmembrane
            domain."

( i x ) FEATURE:

( A ) NAME/KEY: Domain
( B ) LOCATION: 291..311
( D ) OTHER INFORMATION: /note= "Proposed transmembrane
domain."

( i x ) FEATURE:
( A ) NAME/KEY: Domain
( B ) LOCATION: 322..345
( D ) OTHER INFORMATION: /note= "Proposed transmembrane
domain."

( i x ) FEATURE:
( A ) NAME/KEY: Domain
( B ) LOCATION: 373..397
( D ) OTHER INFORMATION: /note= "Proposed transmembrane
domain."

( i x ) FEATURE:
( A ) NAME/KEY: Domain
( B ) LOCATION: 424..443
( D ) OTHER INFORMATION: /note= "Proposed transmembrane
domain."

( i x ) FEATURE:
( A ) NAME/KEY: Domain
( B ) LOCATION: 456..479
( D ) OTHER INFORMATION: /note= "Proposed transmembrane
domain."

( i x ) FEATURE:
( A ) NAME/KEY: Domain
( B ) LOCATION: 500..519
( D ) OTHER INFORMATION: /note= "Proposed transmembrane
domain."

( i x ) FEATURE:
( A ) NAME/KEY: Domain
( B ) LOCATION: 536..559
( D ) OTHER INFORMATION: /note= "Proposed transmembrane
domain."

( i x ) FEATURE:
( A ) NAME/KEY: Active-site
( B ) LOCATION: 76..77
( D ) OTHER INFORMATION: /note= "Leucine zipper motif"

( i x ) FEATURE:
( A ) NAME/KEY: Active-site
( B ) LOCATION: 83..84
( D ) OTHER INFORMATION: /note= "Leucine zipper motif"

( i x ) FEATURE:
( A ) NAME/KEY: Active-site
( B ) LOCATION: 90..91
( D ) OTHER INFORMATION: /note= "Leucine zipper motif"

( i x ) FEATURE:
( A ) NAME/KEY: Active-site
( B ) LOCATION: 97..98
( D ) OTHER INFORMATION: /note= "Leucine zipper motif"

( x i ) SEQUENCE DESCRIPTION: SEQ ID NO:9:

Met Lys Lys Leu Gln Glu Ala His Leu Arg Lys Pro Val Thr Pro Asp
1               5                   10                  15

Leu Leu Met Thr Pro Ser Asp Gln Gly Asp Val Asp Leu Asp Val Asp
                20                  25                  30

Phe Ala Ala Asp Arg Gly Asn Trp Thr Gly Lys Leu Asp Phe Leu Leu
            35                  40                  45

Ser Cys Ile Gly Tyr Cys Val Gly Leu Gly Asn Val Trp Arg Phe Pro
        50                  55                  60

Tyr Arg Ala Tyr Thr Asn Gly Gly Gly Ala Phe Leu Val Pro Tyr Phe
65                  70                  75                  80

Leu Met Leu Ala Ile Cys Gly Ile Pro Leu Phe Phe Leu Glu Leu Ser
                85                  90                  95

```
Leu Gly Gln Phe Ser Ser Leu Gly Pro Leu Ala Val Trp Lys Ile Ser
            100             105                 110
Pro Leu Phe Lys Gly Ala Gly Ala Ala Met Leu Leu Ile Val Gly Leu
        115             120                 125
Val Ala Ile Tyr Tyr Asn Met Ile Ile Ala Tyr Val Leu Phe Tyr Leu
    130             135                 140
Phe Ala Ser Leu Tyr Ser Asn Leu Pro Trp Glu His Cys Gly Asn Trp
145             150                 155                     160
Trp Asn Thr Glu Arg Cys Leu Glu His Arg Gly Pro Lys Asp Gly Asn
                165                 170                 175
Gly Ala Leu Pro Leu Asn Leu Ser Ser Thr Val Ser Pro Ser Glu Glu
            180             185                 190
Tyr Trp Ser Arg Tyr Val Leu His Ile Gln Gly Ser Gln Gly Ile Gly
        195             200                 205
Arg Pro Gly Glu Ile Arg Trp Asn Leu Cys Leu Cys Leu Leu Leu Ala
    210             215                 220
Trp Val Ile Val Phe Leu Cys Ile Leu Lys Gly Val Lys Ser Ser Gly
225             230                 235                     240
Arg Val Val Tyr Phe Thr Ala Thr Phe Pro Tyr Leu Ile Leu Leu Met
                245                 250                 255
Leu Leu Val Arg Gly Val Thr Leu Pro Gly Ala Trp Lys Gly Ile Gln
            260             265                 270
Phe Tyr Leu Thr Pro Gln Phe His His Leu Leu Ser Ser Lys Val Trp
        275             280                 285
Ile Glu Ala Ala Leu Gln Ile Phe Tyr Ser Leu Gly Val Gly Phe Gly
    290             295                 300
Gly Leu Leu Thr Phe Ala Ser Tyr Asn Thr Phe His Gln Asn Ile Tyr
305             310                 315                     320
Arg Asp Thr Phe Ile Val Thr Leu Gly Asn Ala Ile Thr Ser Ile Leu
                325                 330                 335
Ala Gly Phe Ala Ile Phe Ser Val Leu Gly Tyr Met Ser Gln Glu Leu
            340             345                 350
Gly Val Pro Val Asp Gln Val Ala Lys Ala Gly Pro Gly Leu Ala Phe
        355             360                 365
Val Ile Tyr Pro Gln Ala Met Thr Met Leu Pro Leu Ser Pro Phe Trp
    370             375                 380
Ser Phe Leu Phe Phe Glu Met Leu Leu Thr Leu Gly Leu Asp Ser Gln
385             390                 395                     400
Phe Ala Phe Leu Glu Thr Ile Val Ile Ala Val Thr Asp Glu Phe Pro
                405                 410                 415
Tyr Tyr Leu Arg Pro Lys Lys Ala Val Phe Ser Gly Leu Ile Cys Val
            420             425                 430
Ala Met Tyr Leu Met Gly Leu Ile Leu Thr Thr Asp Gly Gly Met Tyr
        435             440                 445
Trp Leu Val Leu Leu Asp Asp Tyr Ser Ala Ser Phe Gly Leu Met Val
    450             455                 460
Val Val Ile Thr Thr Cys Leu Ala Val Thr Arg Val Tyr Gly Ile Gln
465             470                 475                     480
Arg Phe Cys Arg Asp Ile His Met Met Leu Gly Phe Lys Pro Gly Leu
                485                 490                 495
Tyr Phe Arg Ala Cys Trp Leu Phe Leu Ser Pro Ala Thr Leu Leu Ala
            500             505                 510
Leu Leu Val Tyr Ser Ile Val Lys Tyr Gln Pro Ser Glu Tyr Gly Ser
```

|     |     |     |     |     | 515 |     |     |     | 520 |     |     |     | 525 |     |
| --- | --- | --- | --- | --- | --- | --- | --- | --- | --- | --- | --- | --- | --- | --- |
| Tyr | Arg 530 | Phe | Pro | Ala | Met | Ala 535 | Glu | Leu | Leu | Gly | Ile 540 | Leu | Met | Gly | Leu |
| Leu 545 | Ser | Cys | Leu | Met | Ile 550 | Pro | Ala | Gly | Met | Leu 555 | Val | Ala | Val | Leu | Arg 560 |
| Glu | Glu | Gly | Ser | Leu 565 | Trp | Glu | Arg | Leu | Gln 570 | Gln | Ala | Ser | Arg | Pro 575 | Ala |
| Ile | Asp | Trp | Gly 580 | Pro | Ser | Leu | Glu | Glu 585 | Asn | Arg | Thr | Gly | Met 590 | Tyr | Val |
| Ala | Thr | Leu 595 | Ala | Gly | Ser | Gln | Ser 600 | Pro | Lys | Pro | Leu | Met 605 | Val | His | Met |
| Arg | Lys 610 | Tyr | Gly | Gly | Ile | Thr 615 | Ser | Phe | Glu | Asn | Thr 620 | Ala | Ile | Glu | Val |
| Asp 625 | Arg | Glu | Ile | Ala | Glu 630 | Glu | Glu | Glu | Glu | Ser 635 |

(2) INFORMATION FOR SEQ ID NO:10:

(i) SEQUENCE CHARACTERISTICS:
        (A) LENGTH: 599 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: N-terminal (vi) ORIGINAL SOURCE:
        (A) ORGANISM: Rattus
        (F) TISSUE TYPE: Brain - GABA transporter (ix) FEATURE:
        (A) NAME/KEY: Active-site
        (B) LOCATION: 83..84
        (D) OTHER INFORMATION: /note= "Leucine zipper motif"

(ix) FEATURE:
        (A) NAME/KEY: Active-site
        (B) LOCATION: 90..91
        (D) OTHER INFORMATION: /note= "Leucine zipper motif"

(ix) FEATURE:
        (A) NAME/KEY: Active-site
        (B) LOCATION: 97..98
        (D) OTHER INFORMATION: /note= "Leucine zipper motif"

(ix) FEATURE:
        (A) NAME/KEY: Active-site
        (B) LOCATION: 104..105
        (D) OTHER INFORMATION: /note= "Leucine zipper motif"

(xi) SEQUENCE DESCRIPTION: SEQ ID NO:10:

| Met 1 | Ala | Thr | Asp | Asn 5 | Ser | Lys | Val | Ala | Asp 10 | Gly | Gln | Ile | Ser | Thr 15 | Glu |
| --- | --- | --- | --- | --- | --- | --- | --- | --- | --- | --- | --- | --- | --- | --- | --- |
| Val | Ser | Glu | Ala 20 | Pro | Val | Ala | Ser | Asp 25 | Lys | Pro | Lys | Thr | Leu 30 | Val | Val |
| Lys | Val | Gln 35 | Lys | Lys | Ala | Gly | Asp 40 | Leu | Pro | Asp | Arg | Asp 45 | Thr | Trp | Lys |
| Gly | Arg 50 | Phe | Asp | Phe | Leu | Met 55 | Ser | Cys | Val | Gly | Tyr 60 | Ala | Ile | Gly | Leu |
| Gly 65 | Asn | Val | Trp | Arg | Glu 70 | Pro | Tyr | Leu | Cys | Gly 75 | Lys | Asn | Gly | Gly | Gly 80 |

```
Ala Phe Leu Ile Pro Tyr Phe Leu Thr Leu Ile Phe Ala Gly Val Pro
                 85              90              95
Leu Phe Leu Leu Glu Cys Ser Leu Gly Gln Tyr Thr Ser Ile Gly Gly
            100             105             110
Leu Gly Val Met Lys Leu Ala Pro Met Phe Lys Gly Val Gly Leu Ala
        115             120             125
Ala Ala Val Leu Ser Phe Trp Leu Asn Ile Tyr Tyr Ile Val Ile Ile
    130             135             140
Ser Trp Ala Ile Tyr Tyr Leu Tyr Asn Ser Phe Thr Thr Thr Leu Pro
145             150             155             160
Trp Lys Gln Cys Asp Asn Pro Trp Asn Thr Asp Arg Cys Phe Ser Asn
                165             170             175
Tyr Ser Leu Val Asn Thr Thr Asn Met Thr Ser Ala Val Val Glu Phe
            180             185             190
Trp Glu Arg Asn Met His Gln Met Thr Asp Gly Leu Asp Lys Pro Gly
        195             200             205
Gln Ile Arg Trp Pro Leu Ala Ile Thr Leu Ala Ile Ala Trp Val Leu
    210             215             220
Val Tyr Phe Cys Ile Trp Lys Gly Val Gly Trp Thr Gly Lys Val Val
225             230             235             240
Tyr Phe Ser Ala Thr Tyr Pro Tyr Ile Met Leu Ile Ile Leu Phe Phe
                245             250             255
Arg Gly Val Thr Leu Pro Gly Ala Lys Glu Gly Ile Leu Phe Tyr Ile
            260             265             270
Thr Pro Asn Phe Arg Lys Leu Ser Asp Ser Glu Val Trp Leu Asp Ala
        275             280             285
Ala Thr Gln Ile Phe Phe Asx Tyr Gly Leu Gly Leu Gly Ser Leu Ile
    290             295             300
Ala Leu Gly Ser Tyr Asn Ser Phe His Asn Asn Val Tyr Arg Asp Ser
305             310             315             320
Ile Ile Val Cys Cys Ile Asn Ser Cys Thr Ser Met Phe Ala Gly Phe
                325             330             335
Val Ile Phe Ser Ile Val Gly Phe Met Ala His Val Thr Lys Arg Ser
            340             345             350
Ile Ala Asp Val Ala Ala Ser Gly Pro Gly Leu Ala Phe Leu Ala Tyr
        355             360             365
Pro Glu Ala Val Thr Gln Leu Pro Ile Ser Pro Leu Trp Ala Ile Leu
    370             375             380
Phe Phe Ser Met Leu Leu Met Leu Gly Ile Asp Ser Gln Phe Cys Thr
385             390             395             400
Val Glu Gly Phe Ile Thr Ala Leu Val Asp Glu Tyr Pro Arg Leu Leu
                405             410             415
Arg Asn Arg Arg Glu Leu Phe Ile Ala Ala Val Cys Ile Val Ser Tyr
            420             425             430
Leu Ile Gly Leu Ser Asn Ile Thr Gln Gly Gly Ile Tyr Val Phe Lys
        435             440             445
Leu Phe Asp Tyr Tyr Ser Ala Ser Gly Met Ser Leu Leu Phe Leu Val
    450             455             460
Phe Phe Glu Cys Val Ser Ile Ser Trp Phe Tyr Gly Val Asn Arg Phe
465             470             475             480
Tyr Asp Asn Ile Gln Glu Met Val Gly Ser Arg Pro Cys Ile Trp Trp
                485             490             495
Lys Leu Cys Trp Ser Phe Phe Thr Pro Ile Ile Val Ala Gly Val Phe
```

|  |  |  |  |  | 500 |  |  | 505 |  |  |  | 510 |  |  |
|---|---|---|---|---|---|---|---|---|---|---|---|---|---|---|
| Leu | Phe | Ser | Ala | Val | Gln | Met | Thr | Pro | Leu | Thr | Met | Gly | Ser | Tyr | Val |
|  |  | 515 |  |  |  |  | 520 |  |  |  |  | 525 |  |  |
| Phe | Pro | Lys | Trp | Gly | Gln | Gly | Val | Gly | Trp | Leu | Met | Ala | Leu | Ser | Ser |
|  | 530 |  |  |  |  | 535 |  |  |  |  | 540 |  |  |  |
| Met | Val | Leu | Ile | Pro | Gly | Tyr | Met | Ala | Tyr | Met | Phe | Leu | Thr | Leu | Lys |
| 545 |  |  |  |  | 550 |  |  |  |  | 555 |  |  |  |  | 560 |
| Gly | Ser | Leu | Lys | Gln | Arg | Leu | Gln | Val | Met | Ile | Gln | Pro | Ser | Glu | Asp |
|  |  |  |  | 565 |  |  |  |  | 570 |  |  |  |  | 575 |  |
| Ile | Val | Arg | Pro | Glu | Asn | Gly | Pro | Glu | Gln | Pro | Gln | Ala | Gly | Ser | Ser |
|  |  |  | 580 |  |  |  |  | 585 |  |  |  |  | 590 |  |  |
| Ala | Ser | Lys | Glu | Ala | Tyr | Ile |
|  |  | 595 |  |  |  |  |

(2) INFORMATION FOR SEQ ID NO:11:

(i) SEQUENCE CHARACTERISTICS:
      (A) LENGTH: 617 amino acids
      (B) TYPE: amino acid
      (C) STRANDEDNESS: single
      (D) TOPOLOGY: linear (ii) MOLECULE TYPE: protein (iii) HYPOTHETICAL: NO (iv) ANTI-SENSE: NO (v) FRAGMENT TYPE: N-terminal (vi) ORIGINAL SOURCE:
      (A) ORGANISM: Homo sapiens
      (F) TISSUE TYPE: Brain - norepinephrine transporter (ix) FEATURE:
      (A) NAME/KEY: Active-site
      (B) LOCATION: 95..96
      (D) OTHER INFORMATION: /note= "Leucine zipper motif"

(ix) FEATURE:
      (A) NAME/KEY: Active-site
      (B) LOCATION: 102..103
      (D) OTHER INFORMATION: /note= "Leucine zipper motif"

(ix) FEATURE:
      (A) NAME/KEY: Active-site
      (B) LOCATION: 109..110
      (D) OTHER INFORMATION: /note= "Leucine zipper motif"

(ix) FEATURE:
      (A) NAME/KEY: Active-site
      (B) LOCATION: 116..117
      (D) OTHER INFORMATION: /note= "Leucine zipper motif"

(xi) SEQUENCE DESCRIPTION: SEQ ID NO:11:

| Met | Leu | Leu | Ala | Arg | Met | Asn | Pro | Gln | Val | Gln | Pro | Glu | Asn | Asn | Gly |
|---|---|---|---|---|---|---|---|---|---|---|---|---|---|---|---|
| 1 |  |  |  | 5 |  |  |  |  | 10 |  |  |  |  | 15 |  |
| Ala | Asp | Thr | Gly | Pro | Glu | Gln | Pro | Leu | Arg | Ala | Arg | Lys | Thr | Ala | Glu |
|  |  |  | 20 |  |  |  |  | 25 |  |  |  |  | 30 |  |  |
| Leu | Leu | Val | Val | Lys | Glu | Arg | Asn | Gly | Val | Gln | Cys | Leu | Leu | Ala | Pro |
|  |  |  | 35 |  |  |  |  | 40 |  |  |  |  | 45 |  |  |
| Arg | Asp | Gly | Asp | Ala | Gln | Pro | Arg | Glu | Thr | Trp | Gly | Lys | Lys | Ile | Asp |
|  |  | 50 |  |  |  |  | 55 |  |  |  |  | 60 |  |  |  |
| Phe | Leu | Leu | Ser | Val | Val | Gly | Phe | Ala | Val | Asp | Leu | Ala | Asn | Val | Trp |
| 65 |  |  |  |  | 70 |  |  |  |  | 75 |  |  |  |  | 80 |
| Arg | Phe | Pro | Tyr | Leu | Cys | Tyr | Lys | Asn | Gly | Gly | Gly | Ala | Phe | Leu | Ile |
|  |  |  |  | 85 |  |  |  |  | 90 |  |  |  |  | 95 |  |

-continued

| | | | | | | | | | | | | | |
|---|---|---|---|---|---|---|---|---|---|---|---|---|---|
| Pro | Tyr | Thr | Leu 100 | Phe | Leu | Ile | Ile | Ala 105 | Gly | Met | Pro | Leu 110 | Phe | Tyr | Met |
| Glu | Leu | Ala 115 | Leu | Gly | Gln | Tyr | Asn 120 | Arg | Glu | Gly | Ala | Ala 125 | Thr | Val | Trp |
| Lys | Ile 130 | Cys | Pro | Phe | Phe | Lys 135 | Gly | Val | Gly | Tyr | Ala 140 | Val | Ile | Leu | Ile |
| Ala 145 | Leu | Tyr | Val | Gly | Phe 150 | Tyr | Tyr | Asn | Val | Ile 155 | Ile | Ala | Trp | Ser | Leu 160 |
| Tyr | Tyr | Leu | Phe | Ser 165 | Ser | Phe | Thr | Leu | Asn 170 | Leu | Pro | Trp | Thr | Asp 175 | Cys |
| Gly | His | Thr | Trp 180 | Asn | Ser | Pro | Asn | Cys 185 | Thr | Asp | Pro | Lys | Leu 190 | Leu | Asn |
| Gly | Ser | Val 195 | Leu | Gly | Asn | His | Thr 200 | Lys | Tyr | Ser | Lys | Tyr 205 | Lys | Phe | Thr |
| Pro | Ala 210 | Ala | Glu | Phe | Tyr | Glu 215 | Arg | Gly | Val | Leu | His 220 | Leu | His | Glu | Ser |
| Ser 225 | Gly | Ile | His | Asp | Ile 230 | Gly | Leu | Pro | Gln | Trp 235 | Gln | Leu | Leu | Leu | Cys 240 |
| Leu | Met | Val | Val | Val 245 | Ile | Val | Leu | Tyr | Phe 250 | Ser | Leu | Trp | Lys | Gly 255 | Val |
| Lys | Thr | Ser | Gly 260 | Lys | Val | Val | Trp | Ile 265 | Thr | Ala | Thr | Leu | Pro 270 | Tyr | Phe |
| Val | Leu | Phe 275 | Val | Leu | Leu | Val | His 280 | Gly | Val | Thr | Leu | Pro 285 | Gly | Ala | Ser |
| Asn | Gly 290 | Ile | Asn | Ala | Tyr | Leu 295 | His | Ile | Asp | Phe | Tyr 300 | Arg | Leu | Lys | Glu |
| Ala 305 | Thr | Val | Trp | Ile | Asp 310 | Ala | Ala | Thr | Gln | Ile 315 | Phe | Phe | Ser | Leu | Gly 320 |
| Ala | Gly | Phe | Gly | Val 325 | Leu | Ile | Ala | Phe | Ala 330 | Ser | Tyr | Asn | Lys | Phe 335 | Asp |
| Asn | Asn | Cys | Tyr 340 | Arg | Asp | Ala | Leu | Leu 345 | Thr | Ser | Ser | Ile | Asn 350 | Cys | Ile |
| Thr | Ser | Phe 355 | Val | Ser | Gly | Phe | Ala 360 | Ile | Phe | Ser | Ile | Leu 365 | Gly | Tyr | Met |
| Ala | His 370 | Glu | His | Lys | Val | Asn 375 | Ile | Glu | Asp | Val | Ala 380 | Thr | Glu | Gly | Ala |
| Gly 385 | Leu | Val | Phe | Ile | Leu 390 | Tyr | Pro | Glu | Ala | Ile 395 | Ser | Thr | Leu | Ser | Gly 400 |
| Ser | Thr | Phe | Trp | Ala 405 | Val | Val | Phe | Phe | Val 410 | Met | Leu | Leu | Ala | Leu 415 | Gly |
| Leu | Asp | Ser | Ser 420 | Met | Gly | Gly | Met | Glu 425 | Ala | Val | Ile | Thr | Gly 430 | Leu | Ala |
| Asp | Asp | Phe 435 | Gln | Val | Leu | Lys | Arg 440 | His | Arg | Lys | Leu | Phe 445 | Thr | Phe | Gly |
| Val | Thr 450 | Phe | Ser | Thr | Phe | Leu 455 | Leu | Ala | Leu | Phe | Cys 460 | Ile | Thr | Lys | Gly |
| Gly 465 | Ile | Tyr | Val | Leu | Thr 470 | Leu | Leu | Asp | Thr | Phe 475 | Ala | Ala | Gly | Thr | Ser 480 |
| Ile | Leu | Phe | Ala | Val 485 | Leu | Met | Glu | Ala | Ile 490 | Gly | Val | Ser | Trp | Phe 495 | Tyr |
| Gly | Val | Asp | Arg 500 | Phe | Ser | Asn | Asp | Ile 505 | Gln | Gln | Met | Met | Gly 510 | Phe | Arg |
| Pro | Gly | Leu | Tyr | Trp | Arg | Leu | Cys | Trp | Lys | Phe | Val | Ser | Pro | Ala | Phe |

|   |   |   | 515 |   |   |   | 520 |   |   |   | 525 |   |   |
|---|---|---|---|---|---|---|---|---|---|---|---|---|---|
| Leu | Leu | Phe | Val | Val | Val | Ser | Ile | Ile | Asn | Phe | Lys | Pro | Leu | Thr |
|     |     |     | 530 |     |     |     | 535 |     |     |     | 540 |     |     |     |
| Tyr | Asp | Asp | Tyr | Ile | Phe | Pro | Pro | Trp | Ala | Asn | Trp | Val | Gly | Trp | Gly |
| 545 |     |     |     |     | 550 |     |     |     |     | 555 |     |     |     |     | 560 |
| Ile | Ala | Leu | Ser | Ser | Met | Val | Leu | Val | Pro | Ile | Tyr | Val | Ile | Tyr | Lys |
|     |     |     |     | 565 |     |     |     |     | 570 |     |     |     |     | 575 |     |
| Phe | Leu | Ser | Thr | Gln | Gly | Ser | Leu | Trp | Glu | Arg | Leu | Ala | Tyr | Gly | Ile |
|     |     |     | 580 |     |     |     |     | 585 |     |     |     |     | 590 |     |     |
| Thr | Pro | Glu | Asn | Glu | His | His | Leu | Val | Ala | Gln | Arg | Asp | Ile | Arg | Gln |
|     |     | 595 |     |     |     |     | 600 |     |     |     |     | 605 |     |     |     |
| Phe | Gln | Leu | Gln | His | Trp | Leu | Ala | Ile |
|     | 610 |     |     |     |     | 615 |     |     |

( 2 ) INFORMATION FOR SEQ ID NO:12:

( i ) SEQUENCE CHARACTERISTICS:
        ( A ) LENGTH: 607 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( v i ) ORIGINAL SOURCE:
        ( A ) ORGANISM: Rattus
        ( F ) TISSUE TYPE: Brain - serotonin transporter ( i x ) FEATURE:
        ( A ) NAME/KEY: Active-site
        ( B ) LOCATION: 95..96
        ( D ) OTHER INFORMATION: /note= "Leucine zipper motif"

( i x ) FEATURE:
        ( A ) NAME/KEY: Active-site
        ( B ) LOCATION: 102..103
        ( D ) OTHER INFORMATION: /note= "Leucine zipper motif"

( i x ) FEATURE:
        ( A ) NAME/KEY: Active-site
        ( B ) LOCATION: 109..110
        ( D ) OTHER INFORMATION: /note= "Leucine zipper motif"

( i x ) FEATURE:
        ( A ) NAME/KEY: Active-site
        ( B ) LOCATION: 116..117
        ( D ) OTHER INFORMATION: /note= "Leucine zipper motif"

( x i ) SEQUENCE DESCRIPTION: SEQ ID NO:12:

| Met | Val | Phe | Tyr | Arg | Arg | Val | Ser | Pro | Pro | Gln | Arg | Thr | Gly | Gln | Ser |
|---|---|---|---|---|---|---|---|---|---|---|---|---|---|---|---|
| 1 |   |   |   | 5 |   |   |   |   | 10 |   |   |   |   | 15 |   |
| Leu | Ala | Lys | Tyr | Pro | Met | Gly | Thr | Leu | Gln | Ser | Pro | Gly | Thr | Ser | Ala |
|   |   |   | 20 |   |   |   |   | 25 |   |   |   |   | 30 |   |   |
| Gly | Asp | Glu | Ala | Ser | His | Ser | Ile | Pro | Ala | Ala | Thr | Thr | Thr | Leu | Val |
|   |   | 35 |   |   |   |   | 40 |   |   |   |   | 45 |   |   |   |
| Ala | Glu | Ile | Arg | Gln | Gly | Glu | Arg | Glu | Thr | Trp | Gly | Lys | Lys | Met | Asp |
|   | 50 |   |   |   |   | 55 |   |   |   |   | 60 |   |   |   |   |
| Phe | Leu | Leu | Ser | Val | Ile | Gly | Tyr | Ala | Val | Asp | Leu | Gly | Asn | Ile | Trp |
| 65 |   |   |   |   | 70 |   |   |   |   | 75 |   |   |   |   | 80 |
| Arg | Phe | Pro | Tyr | Ile | Cys | Tyr | Gln | Asn | Gly | Gly | Gly | Ala | Phe | Leu | Leu |
|   |   |   |   | 85 |   |   |   |   | 90 |   |   |   |   | 95 |   |

```
Pro Tyr Thr Ile Met Ala Ile Phe Gly Ile Pro Leu Phe Tyr Met
            100                 105                 110
Glu Leu Ala Leu Gly Gln Tyr His Arg Asn Gly Cys Ile Ser Ile Trp
        115                 120                 125
Arg Lys Ile Cys Pro Ile Phe Lys Gly Ile Gly Tyr Ala Ile Cys Ile
    130                 135                 140
Ile Ala Phe Tyr Ile Ala Ser Tyr Tyr Asn Thr Ile Ile Ala Trp Ala
145                 150                 155                 160
Leu Tyr Tyr Leu Ile Ser Ser Leu Thr Asp Arg Leu Pro Trp Thr Ser
                165                 170                 175
Cys Thr Asn Ser Trp Asn Thr Gly Asn Cys Thr Asn Tyr Phe Ala Gln
            180                 185                 190
Asp Asn Ile Thr Trp Thr Leu His Ser Thr Ser Pro Ala Glu Glu Phe
            195                 200                 205
Tyr Leu Arg His Val Leu Gln Ile His Gln Ser Lys Gly Leu Gln Asp
    210                 215                 220
Leu Gly Thr Ile Ser Trp Gln Leu Thr Leu Cys Ile Val Leu Ile Phe
225                 230                 235                 240
Thr Val Ile Tyr Phe Ser Ile Trp Lys Gly Val Lys Thr Ser Gly Lys
                245                 250                 255
Val Val Trp Val Thr Ala Thr Phe Pro Tyr Ile Val Leu Ser Val Leu
            260                 265                 270
Leu Val Arg Gly Ala Thr Leu Phe Gly Ala Trp Arg Gly Val Val Phe
        275                 280                 285
Tyr Leu Lys Pro Asn Trp Gln Lys Leu Leu Glu Thr Gly Val Trp Val
    290                 295                 300
Asp Ala Ala Ala Gln Ile Phe Phe Ser Leu Gly Pro Gly Phe Gly Val
305                 310                 315                 320
Leu Leu Ala Phe Ala Ser Tyr Asn Lys Phe Asn Asn Asn Cys Tyr Gln
                325                 330                 335
Asp Ala Leu Val Thr Ser Val Val Asn Cys Met Thr Ser Phe Val Ser
            340                 345                 350
Gly Phe Val Ile Phe Thr Val Leu Gly Tyr Met Ala Glu Met Arg Asn
        355                 360                 365
Glu Asp Val Ser Glu Val Ala Lys Asp Ala Gly Pro Ser Leu Leu Phe
    370                 375                 380
Ile Thr Tyr Ala Glu Ala Ile Ala Asn Met Pro Ala Ser Thr Phe Phe
385                 390                 395                 400
Ala Ile Ile Phe Phe Leu Met Leu Ile Thr Leu Gly Leu Asp Ser Thr
                405                 410                 415
Phe Ala Gly Leu Glu Gly Val Ile Thr Ala Val Leu Asp Glu Phe Pro
            420                 425                 430
His Ile Trp Ala Lys Arg Arg Glu Trp Phe Val Leu Ile Val Val Ile
        435                 440                 445
Thr Cys Val Leu Gly Ser Leu Leu Thr Leu Thr Ser Gly Gly Ala Tyr
    450                 455                 460
Val Val Thr Leu Leu Glu Glu Tyr Ala Thr Gly Pro Ala Val Leu Thr
465                 470                 475                 480
Val Ala Leu Ile Glu Ala Val Ala Val Ser Trp Phe Tyr Gly Ile Thr
                485                 490                 495
Gln Phe Cys Ser Asp Val Lys Glu Met Leu Gly Phe Ser Pro Gly Trp
            500                 505                 510
Phe Trp Arg Ile Cys Trp Val Ala Ile Ser Pro Leu Phe Leu Leu Phe
```

|       |       |       | 515   |       |       |       | 520   |       |       |       | 525   |       |       |
|-------|-------|-------|-------|-------|-------|-------|-------|-------|-------|-------|-------|-------|-------|
| Ile   | Ile   | Cys   | Ser   | Phe   | Leu   | Met   | Ser   | Pro   | Pro   | Gln   | Leu   | Arg   | Leu   | Phe   | Gln |
|       |       |       | 530   |       |       |       | 535   |       |       |       | 540   |       |       |       |     |
| Tyr   | Asn   | Tyr   | Pro   | His   | Trp   | Ser   | Ile   | Val   | Leu   | Gly   | Tyr   | Cys   | Ile   | Gly   | Met |
| 545   |       |       |       |       | 550   |       |       |       |       | 555   |       |       |       |       | 560 |
| Ser   | Ser   | Val   | Ile   | Cys   | Ile   | Pro   | Thr   | Tyr   | Ile   | Ile   | Tyr   | Arg   | Leu   | Ile   | Ser |
|       |       |       |       | 565   |       |       |       |       | 570   |       |       |       |       | 575   |     |
| Thr   | Pro   | Gly   | Thr   | Leu   | Lys   | Glu   | Arg   | Ile   | Ile   | Lys   | Ser   | Ile   | Thr   | Pro   | Glu |
|       |       |       | 580   |       |       |       |       | 585   |       |       |       |       | 590   |       |     |
| Thr   | Pro   | Thr   | Glu   | Ile   | Pro   | Cys   | Gly   | Asp   | Ile   | Arg   | Met   | Asn   | Ala   | Val   |     |
|       |       | 595   |       |       |       |       | 600   |       |       |       |       | 605   |       |       |     |

( 2 ) INFORMATION FOR SEQ ID NO:13:

( i ) SEQUENCE CHARACTERISTICS:
        ( A ) LENGTH: 616 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( v i ) ORIGINAL SOURCE:
        ( A ) ORGANISM: Rattus
        ( F ) TISSUE TYPE: Brain - dopamine transporter ( i x ) FEATURE:
        ( A ) NAME/KEY: Active-site
        ( B ) LOCATION: 99..100
        ( D ) OTHER INFORMATION: /note= "Leucine zipper motif"

( i x ) FEATURE:
        ( A ) NAME/KEY: Active-site
        ( B ) LOCATION: 106..107
        ( D ) OTHER INFORMATION: /note= "Leucine zipper motif"

( i x ) FEATURE:
        ( A ) NAME/KEY: Active-site
        ( B ) LOCATION: 113..114
        ( D ) OTHER INFORMATION: /note= "Leucine zipper motif"

( i x ) FEATURE:
        ( A ) NAME/KEY: Active-site
        ( B ) LOCATION: 120..121
        ( D ) OTHER INFORMATION: /note= "Leucine zipper motif"

( x i ) SEQUENCE DESCRIPTION: SEQ ID NO:13:

| Met | Ser | Lys | Ser | Lys | Cys | Ser | Val | Gly | Pro | Met | Ser | Ser | Val | Val | Ala |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Pro | Ala | Lys | Glu | Ser | Asn | Ala | Val | Gly | Pro | Arg | Glu | Val | Glu | Leu | Ile |
|     |     |     | 20  |     |     |     |     | 25  |     |     |     |     | 30  |     |     |
| Leu | Val | Lys | Glu | Gln | Asn | Gly | Val | Gln | Leu | Thr | Asn | Ser | Thr | Leu | Ile |
|     |     |     | 35  |     |     |     |     | 40  |     |     |     | 45  |     |     |     |
| Asn | Pro | Pro | Gln | Thr | Pro | Val | Glu | Ala | Gln | Glu | Arg | Glu | Thr | Trp | Ser |
|     | 50  |     |     |     |     | 55  |     |     |     |     | 60  |     |     |     |     |
| Lys | Lys | Ile | Asp | Phe | Leu | Leu | Ser | Val | Ile | Gly | Phe | Ala | Val | Asp | Leu |
| 65  |     |     |     |     | 70  |     |     |     |     | 75  |     |     |     |     | 80  |
| Ala | Asn | Val | Trp | Arg | Phe | Pro | Tyr | Leu | Cys | Tyr | Lys | Asn | Gly | Gly | Gly |
|     |     |     |     | 85  |     |     |     |     | 90  |     |     |     |     | 95  |     |
| Ala | Phe | Leu | Val | Pro | Tyr | Leu | Leu | Phe | Met | Val | Ile | Ala | Gly | Met | Pro |
|     |     |     |     | 100 |     |     |     |     | 105 |     |     |     |     | 110 |     |

-continued

```
Leu Phe Tyr Met Glu Leu Ala Leu Gly Gln Phe Asn Arg Glu Gly Ala
        115                 120                 125
Ala Gly Val Trp Lys Ile Cys Pro Val Leu Lys Gly Val Gly Phe Thr
130                 135                 140
Val Ile Leu Ile Ser Phe Tyr Val Gly Phe Phe Asn Val Ile Ile Ala
145                 150                 155                 160
Trp Ala Leu His Tyr Phe Phe Ser Ser Phe Thr Met Asp Leu Pro Trp
            165                 170                 175
Ile His Cys Asn Asn Thr Trp Asn Ser Pro Asn Cys Ser Asp Ala His
            180                 185                 190
Ala Ser Asn Ser Ser Asp Gly Leu Gly Leu Asn Asp Thr Phe Gly Thr
        195                 200                 205
Thr Pro Ala Ala Glu Tyr Phe Glu Arg Gly Val Leu His Leu His Gln
    210                 215                 220
Ser Arg Gly Ile Asp Asp Leu Gly Pro Pro Arg Trp Gln Leu Thr Ala
225                 230                 235                 240
Leu Val Leu Val Ile Val Leu Leu Tyr Phe Ser Leu Trp Lys Gly Val
                245                 250                 255
Lys Thr Ser Gly Lys Val Val Trp Ile Thr Ala Ile Met Tyr Val Val
            260                 265                 270
Leu Thr Ala Leu Leu Leu Arg Gly Val Ile Leu Pro Gly Ala Met Asp
        275                 280                 285
Gly Ile Arg Ala Tyr Leu Ser Val Asp Phe Tyr Arg Leu Cys Glu Ala
    290                 295                 300
Ser Val Asn Ile Asp Ala Ala Thr Gln Val Cys Phe Ser Leu Gly Val
305                 310                 315                 320
Gly Phe Gly Val Leu Ile Ala Phe Ser Ser Tyr Asn Lys Phe Thr Asn
                325                 330                 335
Asn Cys Tyr Arg Asp Ala Ile Ile Thr Thr Ser Ile Asn Ser Leu Thr
            340                 345                 350
Ser Phe Ser Ser Gly Phe Val Val Phe Ser Phe Leu Gly Tyr Met Ala
        355                 360                 365
Gln Lys His Asn Val Pro Ile Arg Asp Val Ala Thr Asp Gly Pro Gly
    370                 375                 380
Leu Ile Phe Ile Ile Tyr Pro Glu Ala Ile Ala Thr Leu Pro Leu Ser
385                 390                 395                 400
Ser Ala Trp Ala Ala Val Phe Phe Leu Met Leu Leu Thr Leu Gly Leu
                405                 410                 415
Asp Ser Ala Met Gly Gly Met Glu Ser Val Leu Thr Gly Leu Val Asp
            420                 425                 430
Glu Phe Gln Leu Leu His Arg His Arg Glu Leu Phe Thr Leu Gly Ile
        435                 440                 445
Val Leu Ala Thr Phe Leu Leu Ser Leu Phe Cys Val Thr Asn Gly Gly
    450                 455                 460
Ile Tyr Val Phe Thr Leu Leu Asp His Phe Ala Ala Gly Thr Ser Leu
465                 470                 475                 480
Leu Phe Gly Val Leu Ile Glu Ala Ile Gly Val Ala Trp Phe Tyr Gly
                485                 490                 495
Val Gln Gln Phe Ser Asp Asp Ile Lys Gln Met Thr Gly Gln Arg Pro
            500                 505                 510
Asn Leu Tyr Trp Arg Leu Cys Trp Lys Leu Val Ser Pro Cys Phe Leu
        515                 520                 525
Leu Tyr Val Val Val Val Ser Ile Val Thr Phe Arg Pro Pro His Tyr
```

-continued

|  | 530 |  |  |  |  | 535 |  |  |  | 540 |  |  |  |  |
|---|---|---|---|---|---|---|---|---|---|---|---|---|---|---|
| Gly 545 | Ala | Tyr | Ile | Phe | Pro 550 | Asp | Trp | Ala | Asn | Ala 555 | Leu | Gly | Trp | Ile | Ile 560 |
| Ala | Thr | Ser | Ser | Met 565 | Ala | Met | Val | Pro | Ile 570 | Tyr | Ala | Thr | Tyr | Lys 575 | Phe |
| Cys | Ser | Leu | Pro 580 | Gly | Ser | Phe | Arg | Glu 585 | Lys | Leu | Ala | Tyr | Ala 590 | Ile | Thr |
| Pro | Glu | Lys 595 | Asp | His | Gln | Leu | Val 600 | Asp | Arg | Gly | Glu | Val 605 | Arg | Gln | Phe |
| Thr | Leu 610 | Arg | His | Trp | Leu | Leu 615 | Leu |